(12) United States Patent
Isobe

(10) Patent No.: US 8,304,259 B2
(45) Date of Patent: Nov. 6, 2012

(54) LABELING DYE FOR DETECTING BIOMOLECULE, LABELING KIT, AND METHOD FOR DETECTING BIOMOLECULE

(75) Inventor: Shinichiro Isobe, Fukuoka (JP)

(73) Assignee: Shinichiro Isobe, Fukuoka (JP)

( * ) Notice: Subject to any disclaimer, the term of this patent is extended or adjusted under 35 U.S.C. 154(b) by 1184 days.

(21) Appl. No.: 11/989,410

(22) PCT Filed: Jul. 28, 2006

(86) PCT No.: PCT/JP2006/315008
§ 371 (c)(1),
(2), (4) Date: Mar. 12, 2008

(87) PCT Pub. No.: WO2007/013601
PCT Pub. Date: Feb. 1, 2007

(65) Prior Publication Data
US 2011/0195408 A1    Aug. 11, 2011

(30) Foreign Application Priority Data
Jul. 28, 2005 (JP) .................................. 2005-219218
Feb. 2, 2006 (JP) .................................. 2006-025658

(51) Int. Cl.
*G01N 33/53* (2006.01)
*C07H 19/04* (2006.01)
*C12Q 1/68* (2006.01)
*C07H 21/02* (2006.01)

(52) U.S. Cl. ............. 436/800; 435/5; 435/6.1; 435/7.1; 435/7.2; 536/23.1; 536/24.3; 536/26.6

(58) Field of Classification Search ............... 436/5, 6.1, 436/7.1, 7.2; 536/23.1, 24.3, 26.6; 436/800
See application file for complete search history.

(56) References Cited

U.S. PATENT DOCUMENTS
7,015,002 B2 * 3/2006 Isobe ........................... 435/6.16
7,662,555 B2 * 2/2010 Isobe ........................... 435/6.12
2003/0232368 A1  12/2003 Bilton et al.

FOREIGN PATENT DOCUMENTS
| EP | 1 152 008 |   | 11/2001 |
| JP | 9505464 | * | 6/1997 |
| JP | 2004-187563 |  | 7/2004 |
| JP | 2006-180835 |  | 7/2006 |
| JP | 2006-234772 |  | 9/2006 |
| WO | 2005/061657 |  | 7/2005 |
| WO | 2005/062046 |  | 7/2005 |
| WO | 2006-030788 |  | 3/2006 |
| WO | 2006/030788 |  | 3/2006 |

OTHER PUBLICATIONS

S. Tyagi et al., "Molecular Beacons: Probes that Fluoresce upon Hybridization", Nature Biotechnology, vol. 14, Mar. 1996, pp. 303-304.
A. Szymanska et al., "Synthesis and Photophysics of Acridine Derivatives", Chemistry of Heterocyclic Compounds, vol. 36, No. 7, 2000, pp. 801-808.
Database CA [online] Chemical Abstract Service, 2004, S. Masashi et al., "Method for detecting IgG using a peptide possessing the binding activity to IgG or bacteriophage displaying such peptide on its surface", retrieved from STN Database accession No. 2004:549544.
Database WPI Week 200627, Thompson Scientific, London, GB; AN 2006-263056; XP 002551617.
International Search Report issued Oct. 17, 2006 in the International (PCT) Application of which the present application is the U.S. National Stage.
V. R. Iyer et al., "The Transcriptional Program in the Response of Human Fibroblasts to Serum", Science, vol. 283, pp. 83-87, Jan. 1, 1999.
M. N. Stojanovic et al., "Aptamer-Based Folding Fluorescent Sensor for Cocaine", J. Am. Chem. Soc., vol. 123, pp. 4928-4931, 2001.
H. Ueyama et al., "A Novel Potassium Sensing in Aqueous Media with a Synthetic Oligonucleotide Derivative. Fluorescence Resonance Energy Transfer Associated with Guanine Quartet-Potassium Ion Complex Formation", J. Am. Chem. Soc., vol. 124, pp. 14286-14287, 2002.
G. K. Walkup et al., "Design and evaluation of a Peptidyl Fluorescent Chemosensor for Divalent Zinc", J. Am. Chem. Soc., vol. 118, pp. 3053-3054, 1996.

* cited by examiner

*Primary Examiner* — Jezia Riley
(74) *Attorney, Agent, or Firm* — Wenderoth, Lind & Ponack, L.L.P.

(57) ABSTRACT

A labeling dye of the present invention includes a coloring portion comprising an organic EL-dye, a bonding portion to be bonded with a biomolecule and a spacer portion for linking the coloring portion and the bonding portion. The present invention provides a high incorporation ratio and also high fluorescence intensity in solid state.

24 Claims, 7 Drawing Sheets

EL-OSu : 17mer DNA = 1 : 1.2 (molar ratio)

EL-OSu-Sp : 17mer DNA = 1 : 1.2

EL-OSu : 20mer DNA = 1 : 10

EL-OSu-Sp : 20mer DNA = 1 : 1.2

Alexa594-NHS : 20mer DNA = 1 : 10

EL-OSu : 40mer DNA = 1 : 10

EL-OSu-Sp : 40mer DNA = 1 : 1.2

17mer DNA : EL-OSu-Sp = 1: 1.2 ~ 1: 200 (molar ratio)

EL-OSu : BSA = 1 : 5 (molar ratio)

EL-OSu-Sp : BSA = 1 : 5

LABELING DYE FOR DETECTING BIOMOLECULE, LABELING KIT, AND METHOD FOR DETECTING BIOMOLECULE

This application is a U.S. national stage of International Application No. PCT/JP2006/315008 filed Jul. 28, 2006.

TECHNICAL FIELD

The present invention relates to a labeling dye comprising a fluorescence dye for detecting a biomolecule such as nucleic acids, proteins, peptides, saccharides and the like, a labeling kit, and a method for detecting biomolecule.

BACKGROUND ART

Recently, a full view of human genome has been disclosed and post genome researches have been intensively and world widely done aiming for gene therapies and gene diagnosis.

As for the DNA analysis, a sample DNA is analyzed by hybridizing a probe nucleic acid fixed on a microarray substrate with a sample DNA labeled with such as a fluorescence dye and forming a double chain DNA. This method can be done by elongating a nucleic acid labeled with a fluorescence dye by PCR method and by hybridizing on a substrate, and then the fluorescence intensity of the labeled target nucleic acid is measured. Recently, methods such as using a primer having more amino groups than usual or introducing an amino group to DNA have been used.

A fluorescence dye is widely used for labeling. High fluorescence intensity, emission even under dry conditions (solid conditions), water solubility, and the like are required for the fluorescence dye. As the fluorescence dye, for example, Cy3 and Cy5 are used (see, e.g., Science 283, 1 Jan. 1999, pp. 83-87).

DISCLOSURE OF INVENTION

However, the conventional labeling dye has a problem that the ratio of incorporation into a sample RNA or DNA is low. For example, a fluorescence dye of about 200-fold mole excess is generally used for DNA having single reaction site. However, in such a condition, the ratio of incorporation into the sample is about 50 to 60%. Therefore, there are problems that much amount of labeling dye is required, leading inevitably to a highly expensive detection method, and a process to remove the unreacted labeling dye is required, leading inevitably to a long analysis time.

In order to achieve the above-mentioned objective, the inventors, etc. of the present invention have studied hard extensively, and have found that unexpectedly, employing a labeling dye comprising a coloring portion comprising an organic EL-dye, a bonding portion to be bonded with a biomolecule and a spacer portion for linking the coloring portion and the bonding portion, the ratio of incorporation into the sample DNA is drastically increased, thus, the present invention has been completed. That is, a labeling dye for biomolecule in accordance with the present invention comprises a labeling dye for detecting a biomolecule by the fluorescence measurement, wherein the labeling dye is characterized by that it includes an organic EL-dye, a bonding portion to be bonded with a biomolecule and a spacer portion for linking the coloring portion and the bonding portion.

In the present invention, as the preferable organic EL-dye used in the present invention, the compounds being comprised of condensed poly-ring compounds consisting of a 5-membered ring compound containing one or more hetero atom(s), selenium atom(s) or boron atom(s) and a 6-membered ring compound having a conjugate system.

Further, as the condensed poly-ring compounds, an azole derivative represented by the following general formula (1), (2) or (3) can be used.

Formula 1

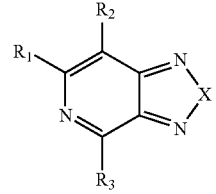

(1)

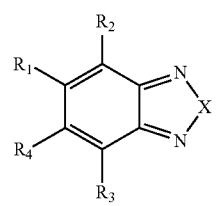

(2)

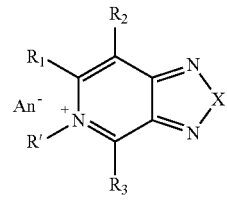

(3)

Here, $R_1$, $R_2$, $R_3$ and $R_4$ represent each independently a hydrogen atom, an aromatic hydrocarbon group, hydrocarbon group, heterocyclic group or aromatic group containing a hetero atom in the ring, optionally having a substituent such as, halogen atom, alkyl group, alkenyl group, alkynyl group, alkoxy group, hydroxyl group, cyano group, sulfonyl group, an aromatic hydrocarbon group, hydrocarbon group, heterocyclic group or aromatic group containing a hetero atom in the ring. X represents a nitrogen atom, sulfur atom, oxygen atom, selenium atom or boron atom. R' represents an aliphatic hydrocarbon group such as alkyl group or alkenyl group, optionally having a substituent such as an aromatic group, or an aromatic hydrocarbon group. $An^-$ represents halide ions such as $Cl^-$, $Br^-$ and $I^-$, $CF_3SO_3^-$, $BF_4^-$ or $PF_6^-$.

As $R_2$ and $R_3$, any one compound selected from the group consisting of a thiophene derivative, furan derivative, pyrole derivative, imidazole derivative, oxazole derivative, thiazole derivative and pyridine derivative can be used.

As $R_2$ and $R_3$, phenyl group having sulfonyl group can also be used.

Further, as the condensed poly-ring compounds, an imidazole derivative represented by the following general formula (4), (5), (6), (7) or (8) can be used.

Formula 2

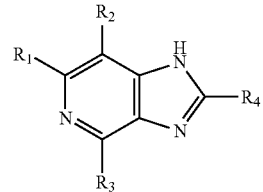

(4)

-continued

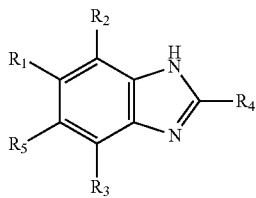

(5)

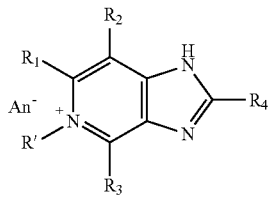

(6)

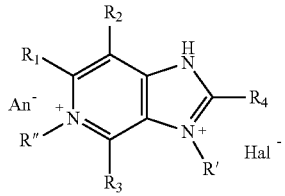

(7)

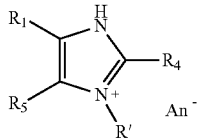

(8)

Here, $R_1$, $R_2$, $R_3$, $R_4$ and $R_5$ represent each independently a hydrogen atom, an aromatic hydrocarbon group, hydrocarbon group, heterocyclic group or aromatic group containing a hetero atom in the ring, optionally having a substituent such as, halogen atom, alkyl group, alkenyl group, alkynyl group, alkoxy group, hydroxyl group, cyano group, sulfonyl group, an aromatic hydrocarbon group, hydrocarbon group, heterocyclic group or aromatic group containing a hetero atom in the ring. $R_1$, $R_2$, $R_3$, $R_4$ and $R_5$ may be the same or different. R' and R" represent an aliphatic hydrocarbon group such as alkyl group or alkenyl group, optionally having a substituent such as an aromatic group, or an aromatic hydrocarbon group. $An^-$ represents halide ions such as $Cl^-$, $Br^-$ and $I^-$, $CF_3SO_3^-$, $BF_4^-$ or $PF_6^-$.

As $R_2$ and $R_3$, any one compound selected from the group consisting of a thiophene derivative, furan derivative, pyrole derivative, imidazole derivative, oxazole derivative, thiazole derivative and pyridine derivative can be used.

As $R_2$ and $R_3$, phenyl group having sulfonyl group can also be used.

Further, as the bonding portion of the labeling dye of the present invention, any one reactive group selected from the group consisting of a carboxyl group, isocyanate group, isothiocyanate group, epoxy group, halogenated alkyl group, triazine group, carbodiimide group and active ester carbonyl group can be used.

Further, as the spacer portion of the labeling dye of the present invention, at least any one functional group selected from the group consisting of —$CH_2$—, —NHCOO—, —CONH—, —$CH_2NH$—, —$CH_2NR$—. —COO—, —$SO_2NH$—, —HN—C(=NH)—NH—, —O—, —S—, —NR—(R represents an alkyl group), —($CH_2$—$CH_2$—O—)$_n$-(n represents an integer of 1 to 10), —CH=CH—, —C≡C—, —Ar— and —CO—Ar—NR— can be used.

As for the spacer portion, the functional group represented by the following general formula (I) can be used.

$$—(CHR')_p—X—(CHR'')_q—$$ (I)

(wherein X represents a direct bond, or at least any one functional group selected from the group consisting of —NHCOO—, —CONH—, —COO—, —$SO_2NH$—, —HN—C(=NH)—NH—, —O—, —S—, —NR—, —CH=CH—, —C≡C—, —Ar— and —CO—Ar—NR—. R' and R" represent each independently a hydrogen atom, an aliphatic hydrocarbon group such as alkyl group or alkenyl group, optionally having a substituent such as aromatic group, or an aromatic hydrocarbon group, and wherein the aliphatic hydrocarbon group or the aromatic hydrocarbon group is optionally substituted with any one charge group selected from the group consisting of sulfonyl group, hydroxyl group, quaternary ammonium group and carboxyl group. Ar represents aryl group. p and q represent each independently an integer of 0 to 20, and the value of "p+q" is greater than or equals to 1.

Further, as the spacer portion, an amino acid or a peptide linker including 2 to 20 amino acids can be used.

Further, when using an amino acid as the spacer portion, a natural amino acid or synthetic amino acid can be used.

Further, as the amino acid, any one selected from the group consisting of cysteine acid, 2-amino-sulfosulfanylpropanic acid, 2-amino-amino-3-sulfoxypropanic acid, tyrosine, threonine, 4-amino-2-hydroxybutanic acid, homo-serine and serine can be used.

Further, when using a peptide linker as the spacer portion, the peptide linker having at least any one charge group selected from the group consisting of sulfonyl group, hydroxyl group, quaternary ammonium group and carboxyl group can be used.

Further, the peptide linker including at least any one amino acid selected from the group consisting of cysteine acid, 2-amino-sulfosulfanylpropanic acid, 2-amino-amino-3-sulfoxypropanic acid, tyrosine, threonine, 4-amino-2-hydroxybutanic acid, homo-serine and serine can also be used.

Further, the first labeling kit for a biomolecule according to the present invention is characterized by that the labeling kit is used to detect the biomolecule by fluorescence measurement, wherein it includes the labeling dye comprising a coloring portion comprising an organic EL-dye, a bonding portion to be bonded with a biomolecule and a spacer portion for linking the coloring portion and the bonding portion, Further, the second labeling kit for a biomolecule according to the present invention is characterized by that the labeling kit is used to detect the biomolecule by fluorescence measurement, wherein it includes the labeling dye comprising a coloring portion comprising an organic EL-dye and a spacer portion bonded with the coloring portion, the spacer portion including at least any one functional group selected from the group consisting of —NHCOO—, —CONH—, —COO—, —$SO_2NH$—, —HN—C(=NH)—NH—, —O—, —S—, —NR—, —CH=CH—, —C≡C—, —Ar— and —CO—Ar—NR—.

Further, the second labeling kit for a biomolecule can include a reactive group introducing reagent to introduce a reactive group selected from the group consisting of a carboxyl group, an isocyanate group, isothiocyanate group, epoxy group, halogenated alkyl group, triazine group, carbodiimide group and active ester carbonyl group into the labeling dye Further, the first method of detecting a biomolecule of the present invention is characterized by that the method comprises of reacting a biomolecule sample with a labeling dye comprising a coloring portion including an organic EL-dye, a bonding portion to be bonded with a biomolecule and a spacer portion for linking the coloring portion and the bonding portion and measuring the fluorescence of the labeled biomolecule. As the biomolecule sample, any one selected from the group consisting of nucleic acids, proteins, peptides and saccharides can be used. Further, proteins can also include an antibody.

The second method of detecting a biomolecule according to the present invention is characterized by that the method comprises of reacting a biomolecule sample with a probe labeled with a labeling dye comprising a coloring portion including an organic EL-dye, a bonding portion to be bonded with a biomolecule and a spacer portion for linking the coloring portion and the bonding portion and measuring the fluorescence of the labeled biomolecule. The above biomolecule can include a nucleic acid while the above probe can include an oligonucleotide or PNA having base sequence(s) complementary to the base sequence of the nucleic acid. Alternatively, when the above oligonucleotide is a primer or terminator, a method of measuring fluorescence of the product obtained by amplifying the above nucleic acid can be used. Alternatively, the primer can be labeled with an organic EL-dye prior to amplifying the nucleic acid. Furthermore, the above oligonucleotide or PNA can be comprised of a molecular beacon.

The third method of detecting a biomolecule according to the present invention is used to detect a sample comprising a biomolecule or sample modified with a modifier, the method is characterized by that the method comprises of reacting a bonding material to be specifically bonded with the sample or bonding material to be specifically bonded with the modifier and a labeling dye comprising a coloring portion including an organic EL-dye, a bonding portion to be bonded with a biomolecule and a spacer portion for linking the coloring portion and the bonding portion and measuring the fluorescence of the labeled biomolecule. As for the combination of the sample or modifier and the binding material, such as antigen and antibody, hapten and anti-hapten antibody, biotin and avidin, Tag and anti-Tag antibody, lectin and glycoprotein, or hormone and receptor can be used.

The fourth method of detecting a biomolecule according to the present invention is characterized by that the method comprises of size separating a biomolecule sample by electrophoresis, wherein the biomolecule sample is labeled with a labeling dye comprising a coloring portion including an organic EL-dye, a bonding portion to be bonded with a biomolecule and a spacer portion for linking the coloring portion and the bonding portion prior to the electrophoresis or after the electrophoresis. The biomolecule sample is a nucleic acid, and base sequence(s) of the nucleic acid can be determined based on the electrophoresis image of the labeled nucleic acid. Alternatively, the biomolecule sample is a protein, and the protein removed from the sample based on the electrophoresis image can be identified by mass analysis.

The dyeing method according to the present invention is characterized by that the method comprises of labeling a biomolecule of tissues or cells with a labeling dye comprising a coloring portion including an organic EL-dye, a bonding portion to be bonded with a biomolecule and a spacer portion for linking the coloring portion and the bonding portion. The above biomolecules may include a nucleic acid or protein.

Further, the chromatic dye used for dyeing tissues or cells according to the present invention is characterized by that the labeling dye comprises a coloring portion comprising an organic EL-dye, a bonding portion to be bonded with a biomolecule and a spacer portion for linking the coloring portion and the bonding portion.

According to the present invention, use of an organic EL-dye as a coloring portion and to introduce a spacer portion between the bonding portion and the coloring portion gives a high incorporation ratio of nearly 100% and also high fluorescence intensity in solid state.

That is, it is deemed that by introducing the spacer portion, the steric hindrance between the coloring portion and the labeling target of biomaterial can be suppressed and the bonding portion can easily bond with the labeling site of biomaterial, leading to the high incorporation ratio. So, according to the labeling dye of the present invention, the high incorporation ratio can be obtained by adjusting the length of the spacer portion, while unaffected by the depth of the labeling site of biomolecule. Accordingly, much amount of labeling dye can be decreased, and thereby to deeply cut in the cost for detecting the target molecule.

Furthermore, an organic EL-dye shows high quantum yield in solid state (including solid state and semi-solid state) and manifests high fluorescence intensity in drying condition such as on the substrate (e.g. microarray) or on the beads. Since an organic EL-dye is cheap as compared with Cy3 and Cy5, a biomolecule can be detected at lower cost.

Furthermore, as excitation wavelength and fluorescence wavelength can be changed by changing the species of substituent of the organic EL-dye, the degree of freedom of selectivity of fluorescence wavelength can be increased and multiple fluorescence wavelengths of orange, yellow, green, blue and the like can be used. By this, it becomes possible to use two or more fluorescence dyes having large stokes shift (large difference between excitation wavelength and fluorescence wavelength), consequently, plural target nucleic acids contained in one sample can also be simultaneously detected. While Cy3 and Cy5 need to be kept in refrigerated state, an organic EL-dye is chemically stable and can be kept for a long time at ambient temperature, therefore, handling thereof is easy.

BEST MODE FOR CARRYING OUT THE INVENTION

Figure 1:
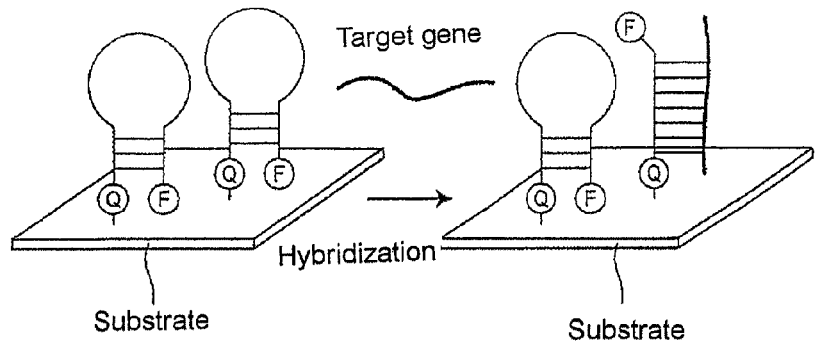
FIG. 1 is a schematic diagram showing a luminescence mechanism in a detection method of the present invention when a molecular beacon is used as a probe.

Hereafter, embodiments of the present invention will be explained in detail.

The labeling dye for biomolecule in accordance with the present invention is characterized by that it includes a coloring portion comprising an organic EL-dye, a bonding portion to be bonded with a biomolecule and a spacer portion for linking the coloring portion and the bonding portion.

The organic EL-dye used in the present invention is not particularly limited provided it is a dye sandwiched in solid state between a pair of anode and cathode and capable of emitting by virtue of energy in recombination of a hole injected from an anode and an electron injected from a cathode. For example, poly-ring aromatic compounds such as tetraphenylbutadiene, perylene and the like, cyclopentadiene derivatives, distyrylpyrazine derivatives, acridone derivatives, quinacridone derivatives, stilbene derivatives, phenothiazine derivatives, pyradinopyridine derivatives, azole derivatives, imidazole derivatives, carbazole derivatives, tetraphenylthiophene derivatives and the like can be used. Further, a dye having a carboxyl group in the molecule or into which a carboxyl group can be introduced is preferable. The reason for this is that a reactive group for bonding with a biomolecule can be introduced easily as described below.

It is preferable that the bonding portion of the labeling dye in the present invention has a reactive group for bonding with a biomolecule sample (hereinafter, referred to target molecule) and the reactive group has a substituent group, nucleophilic reagent or electrophilic reagent capable of reacting with the target molecule and forming covalent bond or ionic bond between the reactive group and the target molecule.

When forming the covalent bond between a labeling dye and a biomolecule, it is preferable that the reactive group has a functional group capable of reacting with an amino group, imino group, thiol group or hydroxyl group of the target molecule.

It is preferable that an amide bond, imide bond, urethane bond, ester bond or guanidine bond is formed between a labeling dye and a biomolecule. As the functional group, for example, an isocyanate group, isothiocyanate group, epoxy group, halogenated sulfonyl group, acyl chloride group, halogenated alkyl group, glyoxal group, aldehyde group, triazine group, carbodiimide group and active ester carbonyl group and the like may be used. It is preferable that any one selected from the group consisting of an isocyanate group, isothiocyanate group, epoxy group, halogenated alkyl group, triazine group, carbodiimide group and active ester carbonyl group is used. The reason for this is that it can form an amide bond with an amino group in a target molecule and can directly bind to an imino group in a biomolecule. Further preferable is a triazine group, carbodiimide group or active ester carbonyl group. When these organic EL-dyes have a carboxyl group, an amino group and imino group present in a biomolecule can also be modified directly in the presence of a carbodiimide derivative and triazine derivative. Further, an organic EL-dye having a triazine group with an optional substituent or a carbodiimide group with an optional substituent can react directly with an imino group of guanine and thymine in DNA bases, therefore, introduction of a dye by a PCR (polymerase chain reaction) method is not necessary, and application thereof to mismatch detection and the like is possible.

When forming the ionic bond between a labeling dye and a biomolecule, it is preferable that the reactive group is an anionic group such as sulfonyl group and carboxyl group. These anionic groups can bond with a cationic group such as amino group and form the ionic bond.

Further, as the reactive group, both of a reactive group to form the covalent bond and reactive group to form ionic bond can be used. This can form the stronger bond between the target molecule and the labeling dye. The combination of the reactive group to form the covalent bond and the reactive group to form ionic bond is not particularly limited. For example, the combination of the above functional group and the anionic group such as the above sulfonyl group or carboxyl group can be used.

In case that the target molecule is DNA, the reactive group can react with the amino acid residue of oligo-DNA terminal, and in case that the target molecule is protein, the reactive group can react with the amino acid residue, and in case that the target molecule is peptide, the reactive group can react with the amino group of polypeptide such as the amino acid residue of poly-lysine derivatives, and in case that the target molecule is saccharide, the reactive group can react with the amino group of polysaccharide derivatives skeleton.

The spacer portion of the labeling dye of the present invention is a part for linking the coloring portion and the reactive group and includes covalent bond or chain of atoms. For example, at least any one functional group selected from the group consisting of —$CH_2$—, —NHCOO—, —CONH—, —$CH_2$NH—, —$CH_2$NR—. —COO—, —$SO_2$NH—, —HN—C(=NH)—NH—, —O—, —S—, —NR—(R represents an alkyl group), —($CH_2$—$CH_2$—O—)$_n$—(n represents an integer of 1 to 10), —CH=CH—, —C≡C—, —Ar— and —CO—Ar—NR— can be used.

That is, one functional group selected in the above group or more than or equal to two functional group selected in the above group can be used as the spacer portion. Further, more than or equal to two functional group of the same species can be used.

For example, in case that the spacer portion includes one functional group, it is preferable to use —CONH—, —COO—, —$CH_2$—O—R—, —$CH_2$NH— and the like. Further, in case that the spacer portion includes more than or equal to two functional group, the following combination can be used.

(1) Two Functional Groups

It is preferable to use —CONH—COO—, —$CH_2$—O—, —$CH_2$—NR— and the like.

(2) More than or Equal to Three Functional Groups (i) It is preferable to use the functional groups described as the following general formula (I).

—(CHR1)$_p$—X—(CHR2)$_q$—      (I)

In the formula, X represents a direct bond or at least any one functional group selected from the group consisting of —NHCOO—, —CONH—, —COO—, —SO$_2$NH—, —HN—C(=NH)—NH—, —O—, —S—, —NR—, —CH=CH—, —C≡C—, —Ar— and —CO—Ar—NR—. It is preferable to use —COO—, —CONH—, —O—, —CH=CH—, —C≡C— or —Ar— and more preferable to use —COO—, —CONH— —O— or —Ar—. R1 and R"2 represent each independently a hydrogen atom, an aliphatic hydrocarbon group such as alkyl group or alkenyl group, optionally having a substituent such as aromatic group, or an aromatic hydrocarbon group, wherein the aliphatic hydrocarbon group or the aromatic hydrocarbon group is optionally substituted with any one charge group selected from the group consisting of sulfonyl group, hydroxyl group, quaternary ammonium group and carboxyl group. Ar represents aryl group, preferably represents phenylene group or naphthylene group, optionally substituted with sulfonyl group. p and q represent each independently an integer of 0 to 20, preferably represents an integer of 0 to 10, more preferably represents an integer of 0 to 5, and the value of "p+q" is greater than or equals to 1.

As the spacer portion, for example, —(CH$_2$)$_p$—CONH—(CH$_2$)q-, —(CH$_2$)p-COO—(CH$_2$)q-, —(CH$_2$)p-CH(—R1-SO$_3$H)—(CH$_2$)q-, —(CH$_2$)p-CH(—R1-N$^+$H$_3$)—(CH$_2$)q-, —(CH$_2$)p-CH(—R1-COOH)—(CH$_2$)q-, —(CH$_2$)p-CH(—R1-OH)—(CH$_2$)q-, —(CH$_2$)p-(O—CH—)$_n$—(CH$_2$)q-, —(CH$_2$)p-CONH(—R1-SO$_3$H)—(CH$_2$)q-, —(CH$_2$)p-CONH(—R1-SO$_3$H)—(CH$_2$)q-, —(CH$_2$)p-CONH(—R1-N$^+$H$_3$)—(CH$_2$)q-, —(CH$_2$)p-CONH(—R1-OH)—(CH$_2$)q-, —(CH$_2$)p-CONH(—R1-COOH)—(CH$_2$)q-, —(CH$_2$)p-COO—R1(—SO$_3$H)—(CH$_2$)q-, —(CH$_2$)p-COO—R1(—OH)—(CH$_2$)q-, —(CH$_2$)p-COO—R1(—N$^+$H$_3$)—(CH$_2$)q-, —(CH$_2$)p-COO—R1(—COOH)—(CH$_2$)q-, —(CH$_2$)p-Ar—(CH$_2$)q-, —(CH$_2$)p-(Ar—COO)—(CH$_2$)q-, —(CH$_2$)p-(Ar—SO$_3$H)—(CH$_2$)q-, —(CH$_2$)p-(Ar—N$^+$H$_3$)—(CH$_2$)q-, —(CH$_2$)p-(Ar—OH)—(CH$_2$)q-, —(CH$_2$)p-(Ar—COOH)—(CH$_2$)q-, —(CH$_2$)p-C≡C—(CH$_2$)q-, —(CH$_2$)p-C≡C—(CH$_2$)q-, —(CH$_2$)p-NR—(CH$_2$)q-, —(CH$_2$)p-O—(CH$_2$)q-, —(CH$_2$)p-S—(CH$_2$)q-, —(CH$_2$)p-HN—C(=NH)—NH—(CH$_2$)q-, —(CH$_2$)p-CO—Ar—NR—(CH$_2$)q— and the like can be used. It is more preferable to use —(CH$_2$)p-CONH—(CH$_2$)q— or —(CH$_2$)$_p$—COO—(CH$_2$)q—.

(ii) It is preferable to use the functional groups described as the following general formula (II).

—Y—(CHR3)$_r$—Z—      (II)

In the formula, Y and Z represent each independently any one functional group selected from the group consisting of —NHCOO—, —CONH—, —COO—, —SO$_2$NH—, —HN—C(=NH)—NH—, —CH$_2$NH—, —CH$_2$NR—, —O—, —S—, —NR—, —CH=CH—, —C≡C—, —Ar— and —CO—Ar—NR—. It is preferable to use the combination of —CONH— and —COO—, —COO— and —COO—, —COO— and —NR— and the like. R3 represents a hydrogen atom, an aliphatic hydrocarbon group such as alkyl group or alkenyl group, optionally having a substituent such as aromatic group, or an aromatic hydrocarbon group, wherein the aliphatic hydrocarbon group or the aromatic hydrocarbon group is optionally substituted with any one charge group selected from the group consisting of sulfonyl group, hydroxyl group, quaternary ammonium group and carboxyl group. Ar represents aryl group, preferably represents phenylene group or naphthylene group, optionally substituted with sulfonyl group. r represents an integer of 0 to 20, preferably represents an integer of 0 to 10, more preferably represents an integer of 0 to 5. As this spacer portion, for example, —CONH—(CH$_2$)$_r$—COO—, —CONH—CH(—R3-OH)—COO—, —CONH—CH(—R3-COOH)—COO—, —CONH—CH(R3-SO$_3$H)—COO—, —COO—(CH$_2$)r-COO— and the like can be used.

Further, as the spacer portion, an amino acid or a peptide linker including 2 to 20 amino acids can be used. Further, when using an amino acid as the spacer portion, natural amino acid or synthetic amino acid can be used. Here, as the natural amino acid, glycine, alanine, valine, leucine. isoleucine, 4-amino-2-hydroxybutanoic acid, homoserine, serine, threonine, aspartic acid, glutamic acid, asparagine, glutamine, lysine, hydroxylysine, arginine, cysteine, cysteic acid, 2-amino-3-sulfosulfanylpropanoic acid, 2-amino-3-sulfoxypropanoic acid, cystine, methionine, phenylalanine, tyrosine, tryptophan, histidine, proline, 4-hydroxyproline and the like can be used.

The synthetic amino acid includes D-isomer of the above natural amino acids and modified amino acids having at least an amino group and carboxyl group in the molecule.

The modified amino acids can be represented by the general formula of H—N(R1)-(R2-CO)—OH. Here, R1 and R2 represent each independently a hydrocarbon group, aromatic group or heterocyclic group, having a substituent of any one charge group selected from the group consisting of sulfonyl group, hydroxyl group, quaternary ammonium group and carboxyl group, wherein the substituent is substituted through or not through ester, ether, thioester, amido, carbamide or thiocarbamide. Further, the hydrocarbon group, aromatic group or heterocyclic group may be substituted with at least any one atom or group selected from the group consisting of halogen atom, alkyl group, alkenyl group, alkynyl group and alkoxy group.

As the preferable amino acid for the spacer portion of the present invention, an amino acid having sulfonyl group such as cysteic acid, 2-amino-3-sulfosulfanylpropanoic acid, 2-amino-3-sulfoxypropanoic acid, and having hydroxyl group such as tyrosine, threonine, 4-amino-2-hydroxybutanoic acid, homoserine and serine can be used. It is more preferable to use cysteic acid or serine.

As the peptide linker, it is preferable to use dipeptides, tripeptides or tetrapeptides such as —C(—R1)-CONH—C(—R2), —C(—R1)-CONH—C(—R2)-CONH—C(—R3)- or —C(—R1)-CONH—C(—R3)-CONH—C(—R4)-. Here, R1, R2, R3 and R4 represent hydrogen atom or a substituent such as alkyl group having number of 1 to 6 carbon atoms, alcohol group, indole group, hydroxyphenyl group, benzyl group, guanidine group, thioether group, alkylthiol group, imdazole group or alkylamine group. The above peptides include homo- or hetero-peptides. For example, Ala-Ser, Glu-Ala, Glu-Ala-Leu, Gly-Pro, Gly-Pro-Asn, Ile-Val or Ile-Val-Met can be used.

Further, it is preferable that a part of the peptide linker is substituted with at least any one charge group selected from the group consisting of sulfonyl group, hydroxyl group, quaternary ammonium group and carboxyl group, For example, the peptide linker having one or more amino acid having one charge group selected from the above group can be used. Therefore, water-solubility of the labeling dye can be improved. For example, peptide linker having one or more amino acid selected from the group consisting of amino acid having sulfonyl group such as cysteic acid, 2-amino-3-sulfosulfanylpropanoic acid, 2-amino-3-sulfoxypropanoic acid, and amino acid having hydroxyl group such as tyrosine, threonine, 4-amino-2-hydroxybutanoic acid, homoserine and serine can be used.

As the distance between the coloring portion and the target site of biomolecule can be changed by changing the length and structure of the spacer portion, it is possible to suppress the steric hindrance between the biomolecule and the labeling dye. That is, by designing the molecular structure of the labeling dye so as to suppress the steric hindrance while considering the steric structure of the biomolecule such as proteins, peptides or DNA, it is possible to increase the incorporation ratio. Further, it is also possible to increase the steric hindrance against the specific site such as deeply situated target site by introducing the functional group such as —CH=CH—, —C≡C—, —Ar— or —CO—Ar—NR—, which gives the rigid property, into the spacer portion. Therefore, it is possible to discriminate a deep target site from shallow target site by labeling the deep target site with a labeling dye giving less steric hindrance against the deep target site while selectively labeling the target site which gives less steric hindrance, for example, shallow target site, with another labeling dye.

In order to introduce the reactive group into the labeling dye of the present invention, for example, the reaction shown in the following Scheme 1 can be used. Reaction formula (I) shows an example in which an active ester carbonyl group is used as the reactive group and —COO— is used as the functional group of the spacer portion which binds to the reactive group. For example, as the active ester carbonyl group, N-hydroxysuccinimide ester and maleimide ester can be used. By use of N-hydroxysuccinimide, an EL-dye and a target molecule can be bound by an amide bond via an N-hydroxysuccinimide ester using N,N'-dicyclohexylcarbodiimide (DCC) as a condensing agent, as shown in formula I in the following Scheme 1.

Further, reaction formula (II) shows an example that a triazine derivative is used as the active ester carbonyl group and —COO— is used as the functional group of the spacer portion which binds to the reactive group.

Further, reaction formula (III) shows an example in which a carbodiimide group is used as the reactive group and —COO— is used as the functional group of the spacer portion which binds to the reactive group. As the carbodiimide group, carbodiimide reagents such as DCC and 1-cyclohexyl-3-(2-morpholinoethyl)carbodiimide and the like can be used. An EL-dye and a target molecule can be bound by an amide bond via a carbodiimide.

Further, reaction formula (IV) shows an example in which a carbodiimide group or triazine group is previously introduced into the spacer portion, that is, a functional group of the spacer portion which binds to the reactive group plays a reactive group. Accordingly, the labeling dye can be bound directly to an amino group and imino group in a biomolecule without introducing the reactive group into the biomolecule separately.

Scheme 1

Formula 3

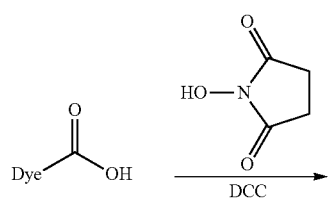

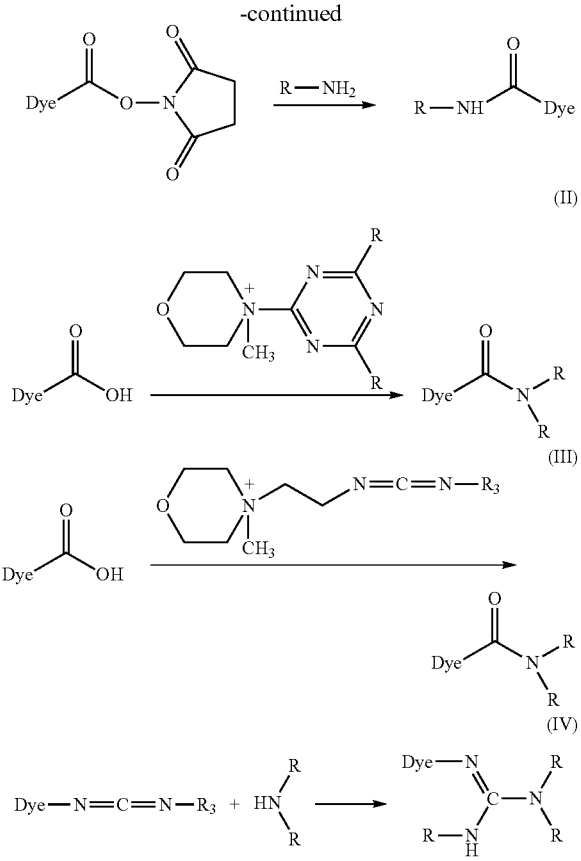

As the preferable organic EL-dye used in the detection method of the present invention, the compounds being comprised of a 5-membered ring compound having a conjugate system and containing one or more hetero atom(s), selenium atom(s) or boron atom(s) are given. Further specifically, a mono-ring compound composed of a 5-membered ring compound having a conjugate system, and a condensed poly-ring compounds consisting of 6-membered ring compound having a conjugate system and the 5-membered ring compound are given. The reason for this is that they have large quantum yield and show intense fluorescence even in solid state.

Specific examples of the condensed poly-ring compound are explained below.

Formula 4

(Mono-azole derivative 1)

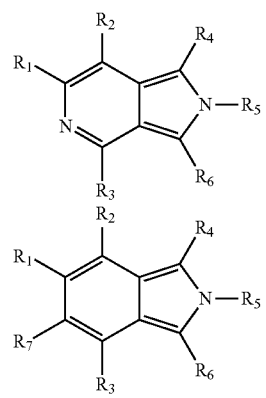

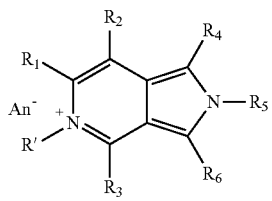
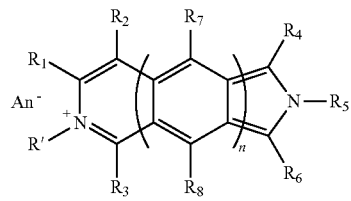

Here, $R_1$, $R_2$, $R_3$, $R_4$, and $R_5$ represent each independently a hydrogen atom, an aromatic hydrocarbon group, hydrocarbon group or heterocyclic group, optionally having a substituent such as, halogen atom, alkyl group, alkenyl group, alkynyl group, alkoxy group, hydroxyl group, cyano group, sulfonyl group, an aromatic hydrocarbon group, hydrocarbon group or heterocyclic group. $R_1$, $R_2$, $R_3$, $R_4$, and $R_5$ may be the same or different. It is preferable that the above alkyl group is a linear or branched alkyl group having 1 to 6 carbon atoms. Further, as the above alkenyl group, a vinyl group, allyl group, tiglyl group or prenyl group is preferable. Further, as the above alkynyl group, an ethynyl group or propargyl group is preferable. Further, as the above alkoxy group, a methoxy group, ethoxy group, propoxy group, isopropoxy group, butoxy group, pentyloxy group or phenoxy group is preferable. Further, the above aromatic hydrocarbon group is a monocyclic or polycyclic group, and a phenyl group, tolyl group, xylyl group or naphthyl group is preferable, and the phenyl group is more preferable. Further, as the above heterocyclic group, a pyrrole group, furan group, thiophene group, imdazole group, oxazole group, thiazole group, pyrazole group, pyridine group or quinoline group is preferable, and the furan group, imidazole group or thiophene group is more preferable. Further, as the above hydrocarbon group, a linear or branched alkyl group having 1 to 6 carbon atoms.

R' represents an aliphatic hydrocarbon group such as alkyl group or alkenyl group optionally having an aromatic ring, or aromatic hydrocarbon group.

An⁻ represents halide ions such as Cl⁻, Br⁻ and I⁻, $CF_3SO_3^-$, $BF_4^-$ or $PF_6^-$. These are the same also in the following general formulae unless otherwise stated.

$R_8$ and $R_9$ represent each independently a hydrogen atom, an aromatic hydrocarbon group, hydrocarbon group or heterocyclic group, optionally having a substituent such as, halogen atom, alkyl group, alkenyl group, alkynyl group, alkoxy group, hydroxyl group, cyano group, sulfonyl group, an aromatic hydrocarbon group or hydrocarbon group, heterocyclic group. $R_8$ and $R_9$ may be the same or different. It is preferable that the above alkyl group is a linear or branched alkyl group having 1 to 6 carbon atoms. Further, as the above alkenyl group, a vinyl group, allyl group, tiglyl group or prenyl group is preferable. Further, as the above alkynyl group, an ethynyl group or propargyl group is preferable. Further, as the above alkoxy group, a methoxy group, ethoxy group, propoxy group, isopropoxy group, butoxy group, pentyloxy group or phenoxy group is preferable. Further, the above aromatic hydrocarbon group is a monocyclic or polycyclic group, and a phenyl group, tolyl group, xylyl group or naphthyl group is preferable, and the phenyl group is more preferable. Further, as the above heterocyclic group, a pyrrole group, furan group, thiophene group, imdazole group, oxazole group, thiazole group, pyrazole group, pyridine group or quinoline group is preferable, and the furan group, imidazole group or thiophene group is more preferable. Further, as the above hydrocarbon group, a linear or branched alkyl group having 1 to 6 carbon atoms.

These are the same also in the following general formulae unless otherwise stated, wherein, n represents an integer of 1 or more, preferably of 1 to 5. This is the same also in the following general formulae.

Formula 5

(Mono-azole derivative 2)

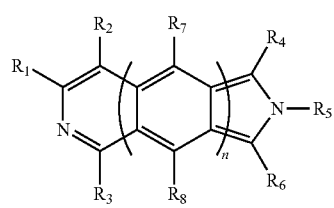

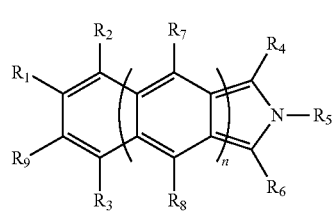

Formula 6

(Diazole derivative 1)

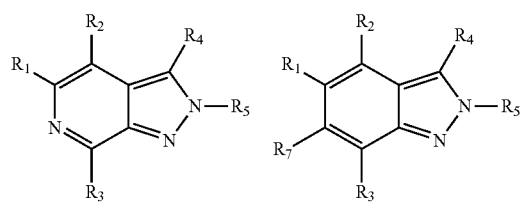

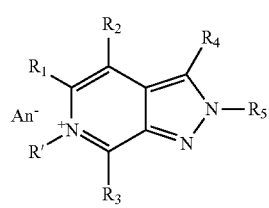

-continued

Formula 7

(Diazole derivative 2)

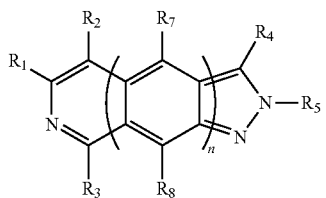

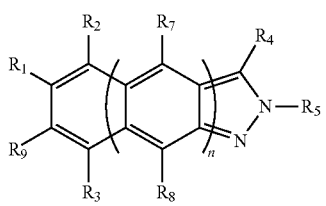

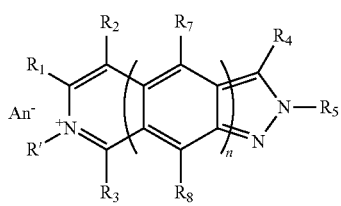

Formula 8

(Diazole derivative 3)

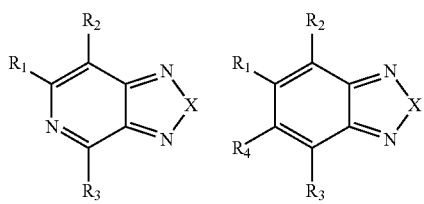

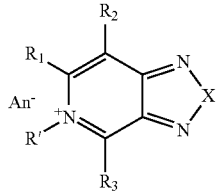

Formula 9

(Diazole derivative 4)

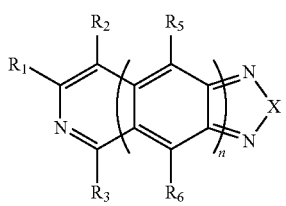

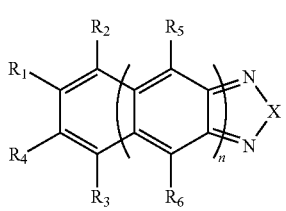

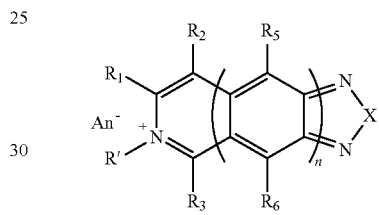

Formula 10

(Diazole derivative 5)

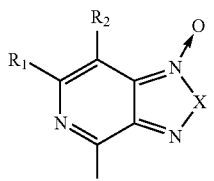

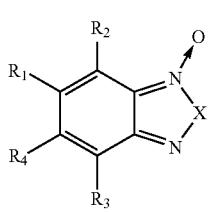

$R_1$, $R_2$, $R_3$ and $R_4$ represent each independently a hydrogen atom, an aromatic hydrocarbon group, hydrocarbon group or heterocyclic group, optionally having a substituent such as, halogen atom, alkyl group, alkenyl group, alkynyl group, alkoxy group, hydroxyl group, cyano group, sulfonyl group, an aromatic hydrocarbon group or hydrocarbon group, heterocyclic group. $R_1$, $R_2$, $R_3$, $R_4$, $R_6$ and $R_7$ may be the same or different. As $R_2$ and $R_3$, aromatic hydrocarbon groups optionally having a substituent are preferable, and as this substituent, alkyl groups and alkoxy groups having 1 to 4 carbon atoms, or a bromine atom are preferable. Further, as the alkyl group, a methyl group, and as the alkoxy group, a methoxy group, are preferably used, respectively. X represents a nitrogen atom, sulfur atom, oxygen atom, selenium atom or boron atom, optionally having a substituent. This is the same also in the following general formulae unless otherwise stated.

N→O represents a state in which a nitrogen atom is coordinate-bonded to an oxygen atom.

Formula 11
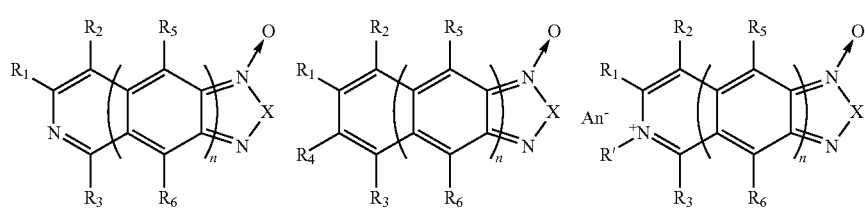
(Diazole derivative 6)
Formula 12
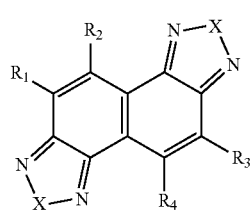
(Diazole derivative 7)
Formula 13-1
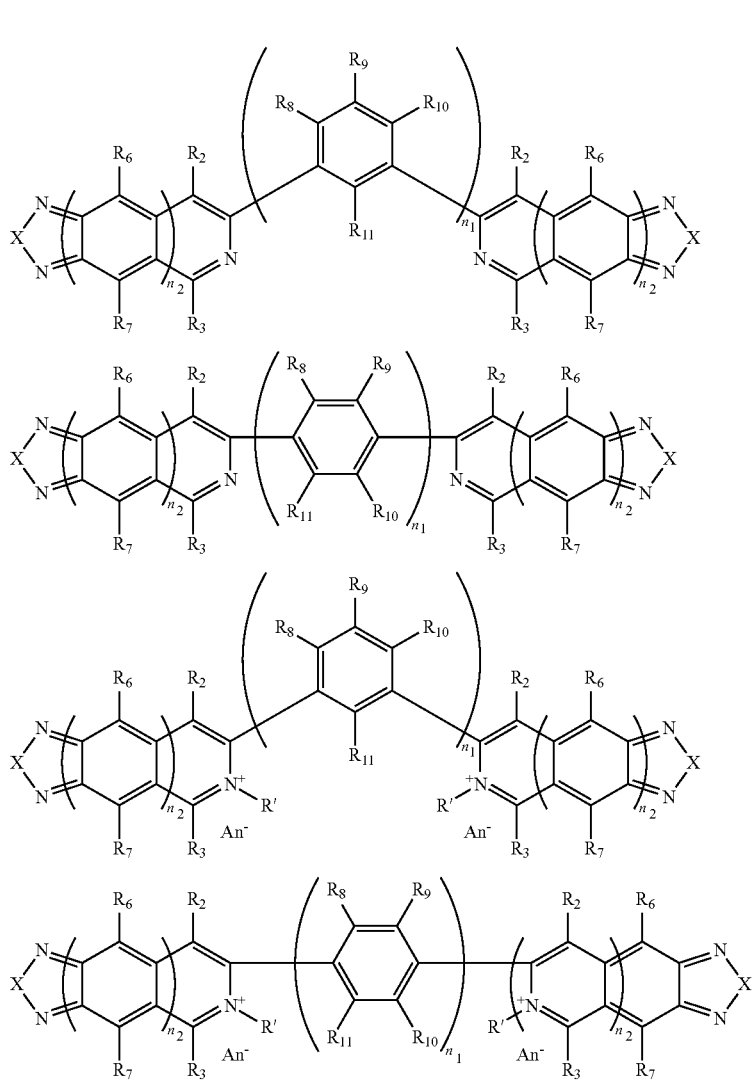
(Diazole derivative 8)

Formula 13-2

-continued

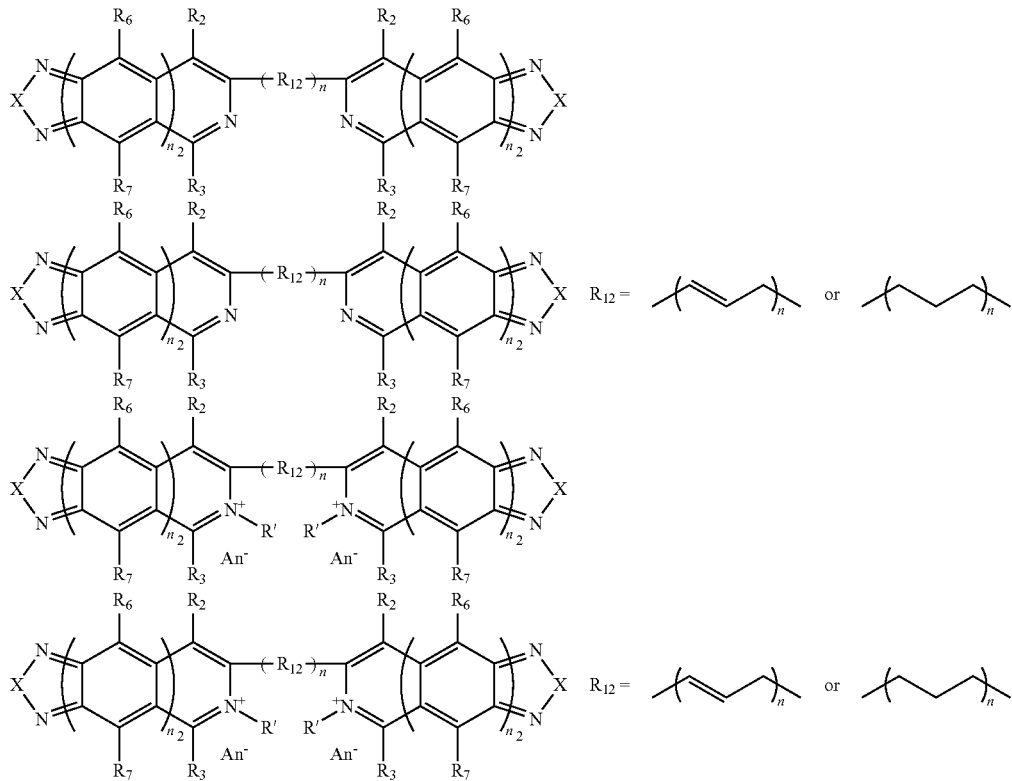

$R_{10}$ and $R_{11}$ represent each independently a hydrogen atom, an aromatic hydrocarbon group, hydrocarbon group or heterocyclic group, optionally having a substituent such as, halogen atom, alkyl group, alkenyl group, alkynyl group, alkoxy group, hydroxyl group, cyano group, sulfonyl group, an aromatic hydrocarbon group or hydrocarbon group, heterocyclic group. $R_{10}$ and $R_{11}$ may be the same or different. It is preferable that the above alkyl group is a linear or branched alkyl group having 1 to 6 carbon atoms. Further, as the above alkenyl group, a vinyl group, allyl group, tiglyl group or prenyl group is preferable. Further, as the above alkynyl group, an ethynyl group or propargyl group is preferable. Further, as the above alkoxy group, a methoxy group, ethoxy group, propoxy group, isopropoxy group, butoxy group, pentyloxy group or phenoxy group is preferable. Further, the above aromatic hydrocarbon group is a monocyclic or polycyclic group, and a phenyl group, tolyl group, xylyl group or naphthyl group is preferable, and the phenyl group is more preferable. Further, as the above heterocyclic group, a pyrrole group, furan group, thiophene group, imdazole group, oxazole group, thiazole group, pyrazole group, pyridine group or quinoline group is preferable, and the furan group, imidazole group or thiophene group is more preferable. Further, as the above hydrocarbon group, a linear or branched alkyl group having 1 to 6 carbon atoms. $R_{12}$ is an olefin group or paraffin group optionally having a substituent, and n represents an integer of 1 to 3, preferably 1. These are the same in the following formulae unless otherwise stated.

Formula 14-1

(Diazole derivative 9)

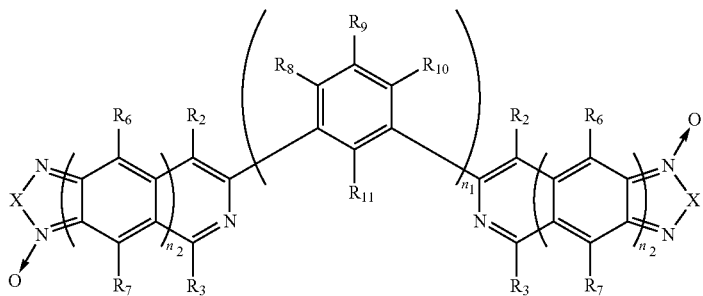

-continued
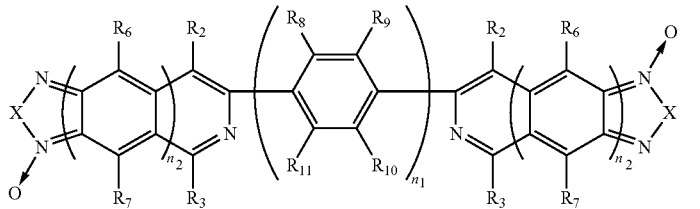
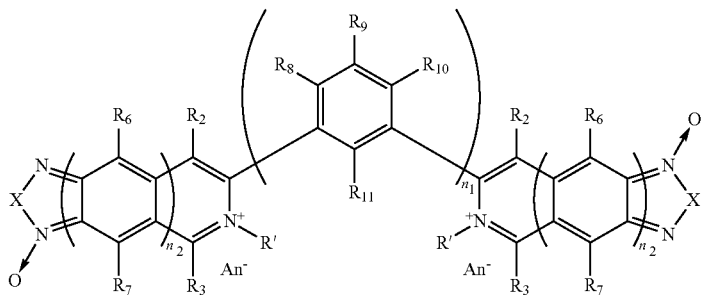
Formula 14-2
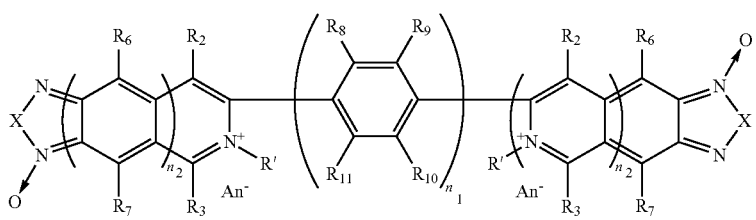
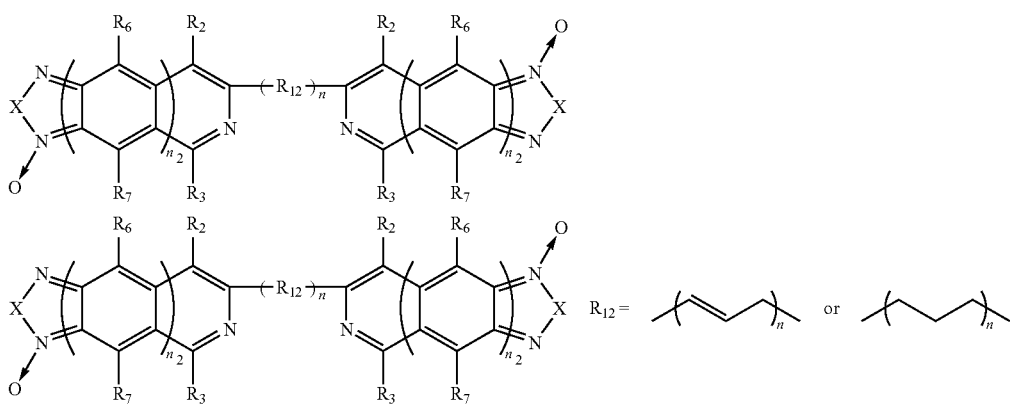
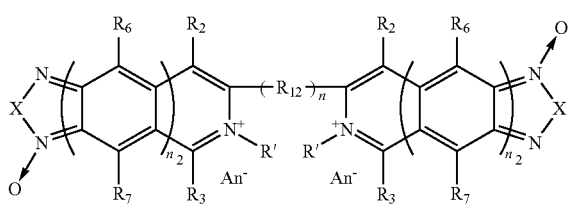
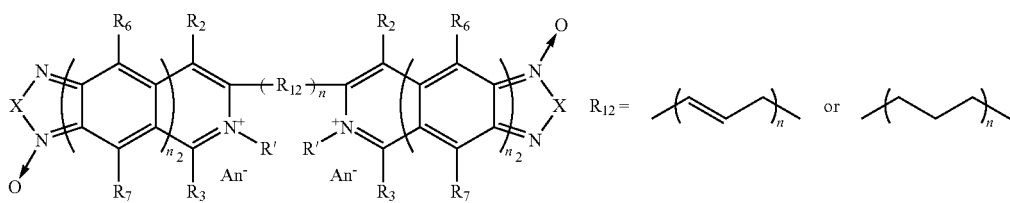

Formula 15

(Triazole derivative 1)

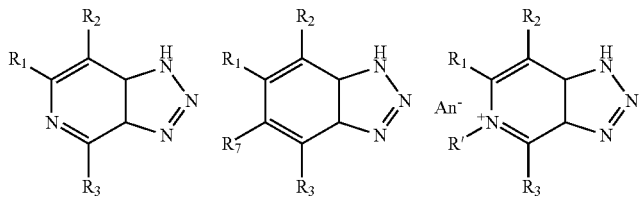

Formula 16

(Triazole derivative 2)

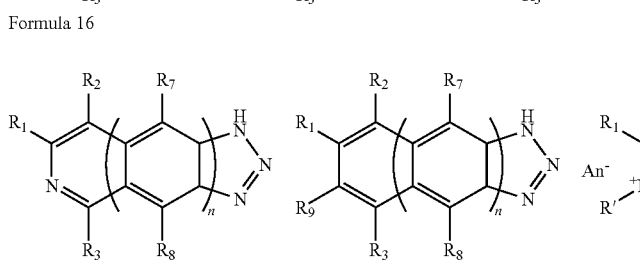

As the 5-membered ring compound, the following derivatives containing a thiophene group can also be used.

Formula 17

(Thiophene derivative 1)

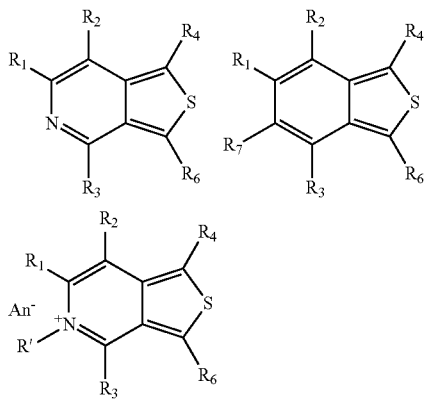

Formula 18

(Thiophene derivative 2)

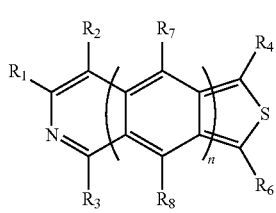

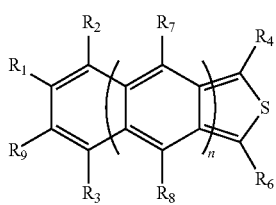

-continued

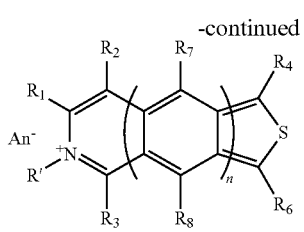

(Thiophene Derivative 3)

In the case of a thiophene derivative, a 2,3,4,5-tetraphenylthiophene derivative which is a non-condensed type compound and represented by the following general formula can also be used.

Formula 19

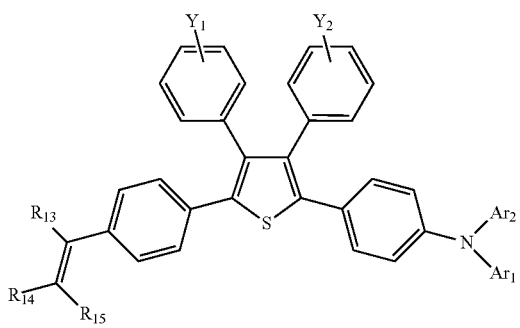

$R_{13}$, $R_{14}$ and $R_{15}$ represent each independently a hydrogen atom, linear-, branched- or cyclic-alkyl group having 1 to 6 carbon atoms, substituted or unsubstituted aryl group, preferably a phenyl group, tolyl group, xylyl group or naphthyl group, or substituted or unsubstituted aralkyl group, preferably a benzyl group or phenethyl group, $Ar_1$ and $Ar_2$ represent a substituted or unsubstituted aryl group, preferably a phenyl group, tolyl group, xylyl group or naphthyl group, further, $Ar_1$ and $Ar_2$ may form a nitrogen-containing heterocyclic ring together with a bonded nitrogen atom. $Y_1$ and $Y_2$ represent a hydrogen atom, halogen atom, linear-, branched- or cyclic-alkyl group having 1 to 6 carbon atoms, linear-, branched- or cyclic-alkoxy group, preferably a methoxy group, ethoxy group, propoxy group, isopropoxy group, butoxy group, pentyloxy group or phenoxy group, substituted or unsubstituted aryl group, preferably a phenyl group, tolyl group, xylyl group or naphthyl group, substituted or unsubstituted aralkyl group, preferably a benzyl group or phenethyl group, or substituted or unsubstituted amino group.

(Thiophene Derivative 4)

A 2,3,4,5-tetraphenylthiophene derivative of the following general formula can also be used.

Formula 20

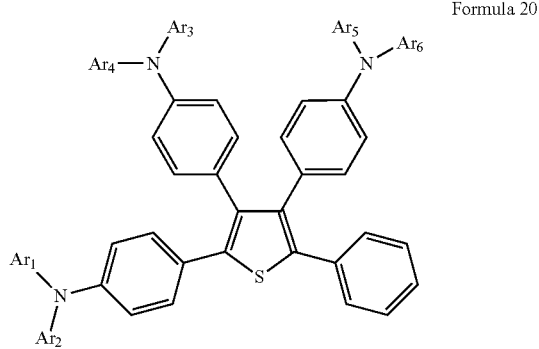

$Ar_1$ to $Ar_6$ represent each independently a substituted or unsubstituted aryl group, preferably a phenyl group, tolyl group, xylyl group or naphthyl group, further, $Ar_1$ and $Ar_2$, $Ar_3$ and $Ar_4$, and $Ar_5$ and $Ar_6$ may form a nitrogen-containing heterocyclic ring together with a bonded nitrogen atom.

Further, an imidazole can also be used as the 5-membered ring compound, for example, imidazole derivatives of the following general formula. Here, it is preferable that an imidazole group of the imidazole derivatives includes a quaternary ammonium group, because the water-solubility can be increased. Furthermore, in case that the imidazole derivatives include a pyridino group, it is preferable that the pyridino group includes a quaternary ammonium group so as to increase the water-solubility. in the following general formula, R" represents an aliphatic hydrocarbon group such as alkyl group or alkenyl group optionally having an aromatic ring, or aromatic hydrocarbon group.

Formula 21

(Imidazole derivative 1)

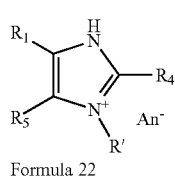

Formula 22

(Imidazole derivative 2)

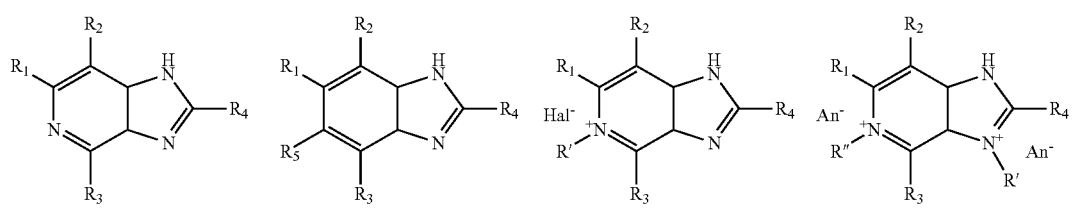

Formula 23

(Imidazole derivative 3)

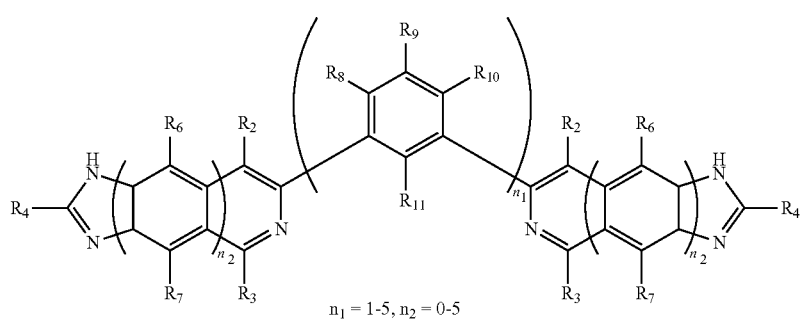

Formula 24

$n_1 = 1\text{-}5, n_2 = 0\text{-}5$

-continued
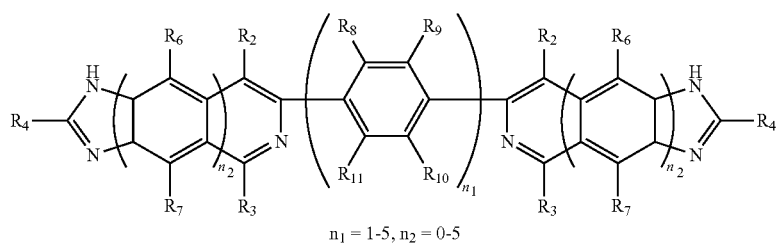
$n_1 = 1\text{-}5,\ n_2 = 0\text{-}5$
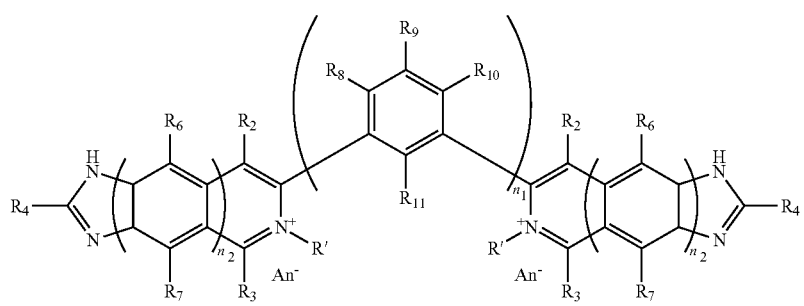
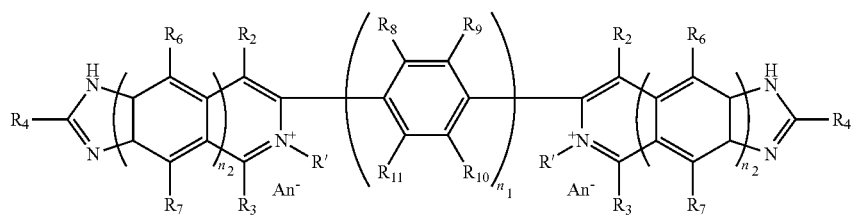
Formula 25
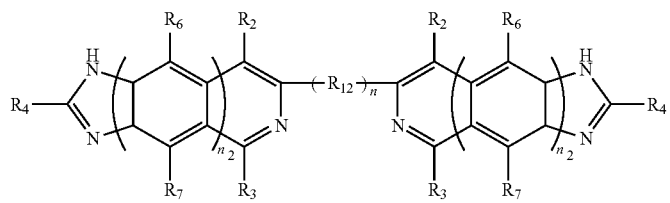
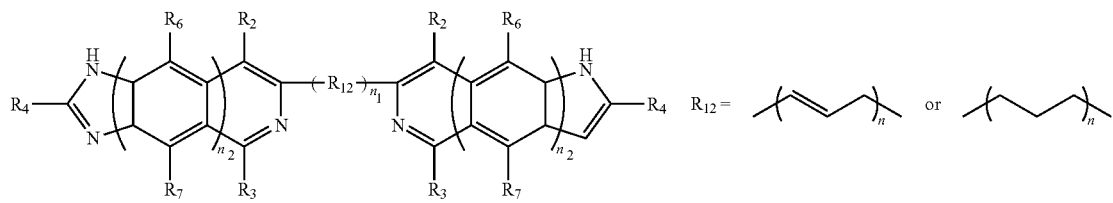
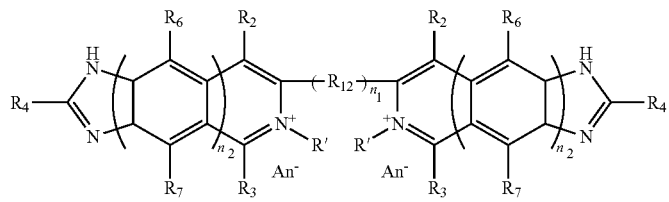
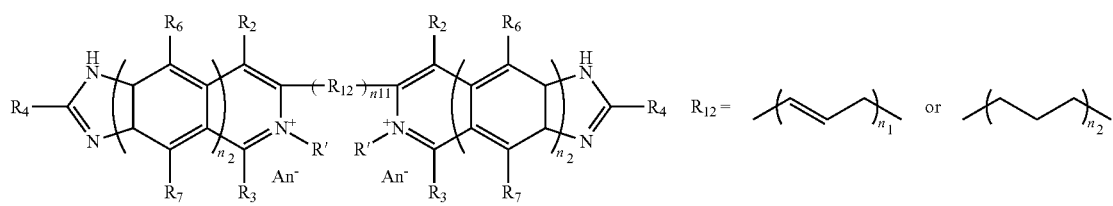

In the imidazole skeleton, a plurality of units may be bonded to any position of center benzene rings $R_8$, $R_9$, $R_{10}$ and $R_{11}$. $R_{12}$ is an olefin group or paraffin group optionally having a substituent, and n represents an integer of 1 to 3, preferably 1.

(Carbazole Derivative)

A carbazole derivative of the following general formula can also be used.

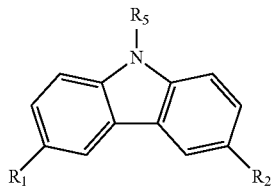

Formula 26

Further, a 5-membered ring compound which is a mono-ring compound having a conjugate system and containing one or more hetero atom(s), selenium atom(s) or boron atom(s) can also be used. Though not particularly limited, azole derivatives of the following general formula, for example, can also be used.

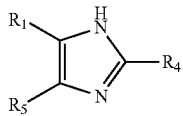

Formula 27

$R_1$, $R_4$ and $R_5$ represent each independently a hydrogen atom, an aromatic hydrocarbon group, hydrocarbon group or heterocyclic group, optionally having a substituent such as, halogen atom, alkyl group, alkenyl group, alkynyl group, alkoxy group, hydroxyl group, cyano group, sulfonyl group, an aromatic hydrocarbon group or hydrocarbon group, heterocyclic group. $R_1$, $R_4$ and $R_5$ may be the same or different. It is preferable that the above alkyl group is a linear or branched alkyl group having 1 to 6 carbon atoms. Further, as the above alkenyl group, a vinyl group, allyl group, tiglyl group or prenyl group is preferable. Further, as the above alkynyl group, an ethynyl group or propargyl group is preferable. Further, as the above alkoxy group, a methoxy group, ethoxy group, propoxy group, isopropoxy group, butoxy group, pentyloxy group or phenoxy group is preferable. Further, the above aromatic hydrocarbon group is a monocyclic or polycyclic group, and a phenyl group, tolyl group, xylyl group or naphthyl group is preferable, and the phenyl group is more preferable. Further, as the above heterocyclic group, a pyrrole group, furan group, thiophene group, imdazole group, oxazole group, thiazole group, pyrazole group, pyridine group or quinoline group is preferable, and the furan group, imidazole group or thiophene group is more preferable. Further, as the above hydrocarbon group, a linear or branched alkyl group having 1 to 6 carbon atoms.

The above-mentioned diazole derivatives are not particularly limited, but an oxadiazolopyridine derivative or imidazole derivative of the following general formulae can be suitably used.

Formula 28

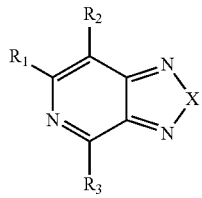 (1)

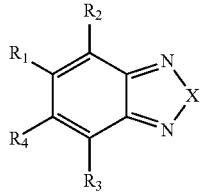 (2)

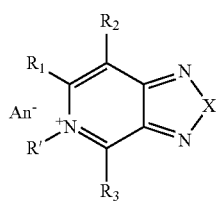 (3)

Formula 29

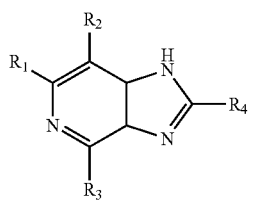 (4)

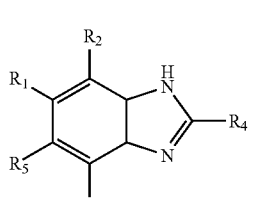 (5)

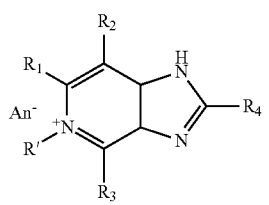 (6)

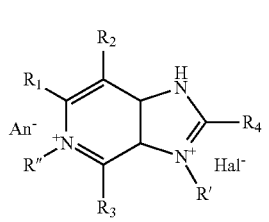 (7)

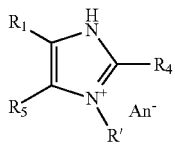

(8)

Further, in the above diazole derivatives or imidazole derivatives, a diazolopyridine derivative or imidazolopyridine derivative can be suitably used.

The labeling dye including the above diazolopyridine derivative or imidazolopyridine derivative as a coloring portion is more preferable and can be represented by the following general formula.

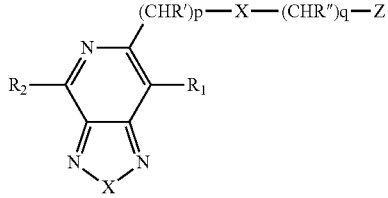

Formula 30

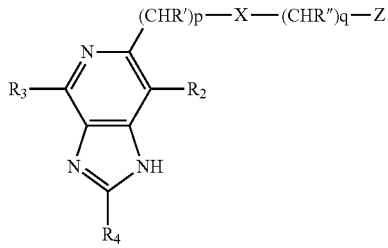

Formula 31

A formula of —(CHR')p-X—(CHR")q- represents the before mentioned spacer portion. Further, z represents the before mentioned reactive group. As R2 and R3, an aromatic hydrocarbon group or hydrocarbon group, optionally having a substituent, can be suitably used. A green labeling dye corresponding to Cy3 can be obtained. Further, as the above aromatic hydrocarbon group, a phenyl group, tolyl group, xylyl group or naphthyl group is preferable, and the phenyl group or tolyl group is more preferable. As the above substituent, a sulfonium group is preferable, because the water-solubility can be increased.

Further, as the above R2 and R3, any one group selected from the group consisting of a thiophene group, furan group, imdazole group, oxazole group, thiazole group, pyrazole group and pyridine group and optionally having a substituent can be used. It is more preferable to use the thiophene group, imdazole group or furan group. A red labeling dye corresponding to Cy5 can be obtained.

The labeling dye of the present invention can be synthesized in various methods by changing the combination of the reactive group and the spacer portion. For example, in case of using an active ester carbonyl group as the reactive group, an active ester of a diazolopyridine derivative or imidazolopyridine derivative is previously synthesized, and the active ester is reacted with a compound for a spacer portion, for example, amino acid such as glycine, alanine, 4-aminobutanoic acid, cysteic acid or serine, to obtain a carboxylic acid, and then the carboxylic acid is reacted with N-hydroxysuccinimide, and thereby to obtain an active ester having the spacer portion. For example, in case of using glycine as the spacer compound, the spacer portion including —CONH— and —(CH$_2$)— can be obtained. Further, in case of using β-alanine as the spacer compound, the spacer portion including —CONH— and —(CH$_2$)$_2$— can be obtained. Further, in case of using 4-aminobutanoic acid as the spacer compound, the spacer portion including —CONH— and —(CH$_2$)$_3$— can be obtained. Further, in case of using cysteic acid as the spacer compound, the spacer portion including —CONH— and —SO$_3^-$ can be obtained. Further, in case of using serine as the spacer compound, the spacer portion including —CONH— and —OH can be obtained. By using cysteic acid or serine as the spacer compound, sulfonium group or hydroxyl group can be introduced into the spacer portion. So, water-solubility of the labeling dye can be increased.

The labeling dye of the present invention can be applied to any method for detection of a biomolecule provided it is a method of measuring the fluorescence of a labeled biomolecule in solid or semi-solid state. By using an organic EL-dye instead of a conventional fluorescence dye, a detection method that provides high sensitivity, chemical stability and excellent handling property as well as low costs can be provided. In the present invention, the biomolecule sample can be labeled with an organic EL-dye by directly reacting the biomolecule sample with an organic EL-dye as mentioned above. Alternatively, a method for labeling a biomolecule sample with an organic EL-dye by reacting a biomolecule sample and a probe labeled with an organic EL-dye can be used. Furthermore, a method comprising size separating a biomolecule sample labeled with an organic EL-dye by electrophoresis can be used.

For example, detection of a nucleic acid using DNA microarray method can be conducted according to the following procedure.

(DNA Micro-Array Method)

In this detection method, the fluorescence of the target nucleic acid is measured by reacting an organic EL-dye with a target nucleic acid to be detected to label the nucleic acid with the organic EL-dye while preparing a probe nucleic acid modified to be a single strand having a base sequence complementary to the target nucleic acid, and hybridizing the target nucleic acid modified to be a single strand and the probe nucleic acid on a substrate. In this detection method, in the case of investigation of a gene expression, a probe nucleic acid prepared by amplifying cDNA, etc. by PCR method using a cDNA library, genome library or whole genome as a template can be used as a probe nucleic acid to be fixed on a substrate. In the case of investigation of a gene mutation, etc., various oligonucleotides corresponding to mutation, etc. those synthesized based on a known sequence as a standard can be used.

A probe nucleic acid can be fixed on a substrate by a suitable method selected depending on the kinds of nucleic acid and substrate. For example, a method in which a probe nucleic acid is electrostatically bound to a substrate whose surface has been treated with cation such as polylysine, etc. utilizing charge of the DNA, can also be used. On the other hand, a target nucleic acid labeled with an organic EL-dye is prepared by mixing a target nucleic acid modified to be a single strand and an organic EL-dye and reacting them. The reaction temperature is preferably from room temperature to 60° C., and the reaction time is preferably from 2 to 48 hours.

Then, the labeled target nucleic acid is spotted on a substrate and hybridized. Hybridization is preferably conducted at room temperature to 70° C. for 2 to 48 hours. By hybridization, a target nucleic acid having a base sequence complementary to a probe nucleic acid is selectively bound to a probe nucleic acid. Thereafter, the substrate is washed and dried at room temperature. The fluorescence intensity of the surface of the dried substrate is then measured by fluorescence laser scanner method. The level of gene expression can be monitored by fluorescence intensity. Although the above-mentioned hybridization is explained based on a method of fixing a probe nucleic acid on a substrate, a method comprising fixing a target nucleic acid that has been labeled with an organic EL-dye in advance on a substrate and spotting a probe nucleic acid on the substrate can also be used.

Similarly, PCR method using a primer and a terminator, which also aims at detecting a nucleic acid, can be carried out by the following procedure.

(PCR Method)

In this detection method, the fluorescence of the target nucleic acid is measured by labeling a probe complementary to the base sequence of the target nucleic acid to be detected with an organic EL-dye, and reacting the target nucleic acid and the probe prior to or after the amplification of the target nucleic acid. Specifically, extension reaction of the target nucleic acid is carried out using an enzyme (DNA polymerase or RNA polymerase). During this reaction, the enzyme recognizes a double stranded nucleic acid sequence formed by the target nucleic acid and a primer comprising an oligonucleotide, and extension reaction is initiated from the recognized position, whereby only the objective gene region is amplified. The synthesis is carried out by the enzyme using a nucleotide (dNTP or NTP) as a raw material. During this reaction, by mixing a nucleotide comprising a dye as shown in FIG. 27 with a general nucleotide (dNTP or NTP) at an arbitral ratio, a nucleic acid in which the dye has been introduced by that ratio can be synthesized. Alternatively, a nucleic acid in which an organic EL-dye has been introduced can be synthesized by introducing a nucleotide having an amino group in an arbitral ratio and binding the organic EL-dye using PCR.

Formula 32

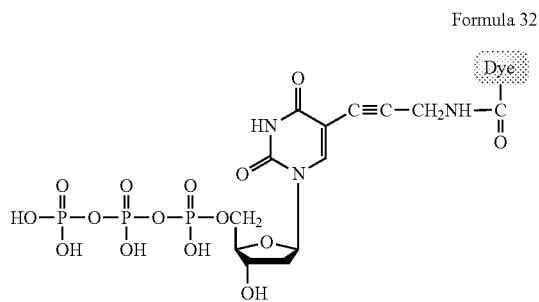

The synthesis by an enzyme is carried out using a nucleotide as a raw material. When a nucleotide in which the OH at 3' position has been substituted with H is used, extension reaction of the nucleic acid does not proceed any more, and at which time the reaction is completed. This nucleotide, dideoxynucleotide triphosphate (ddNTP), is referred to as a terminator. Where the nucleic acid is synthesized by mixing a general nucleotide with a terminator, the terminator is introduced at a constant probability. Therefore, when the reaction is completed, nucleic acids having various lengths are synthesized. These nucleic acids are subjected to size separation by gel electrophoresis, whereby DNAs are aligned in the sequence of length. Where the nucleic acids are labeled with different organic EL-dyes according to the kind of the base in the terminator in advance, a tendency dependent on each base is observed at the end point (3' end) of the synthesis reaction, and the base sequence information of the target nucleic acid can be obtained by reading fluorescence information beginning with the organic EL-dye labeled to the terminator. Alternatively, the nucleic acids can be hybridized to the target nucleic acid using a primer that has been labeled with an organic EL-dye in advance, instead of a terminator.

Alternatively, PNA (peptide nucleic acid) can be used as a probe. PNA is a nucleic acid in which a pentose-phosphoric acid skeleton, which is a basic skeleton structure of a nucleic acid, has been substituted with a polyamide skeleton comprising glycine as a unit, which has a three-dimension structure very similar to that of a nucleic acid, and binds very specifically and strongly to a nucleic acid having a complementary base sequence. Therefore, it is effective as a probe for detection of a specific nucleic acid. Accordingly, PNA can be used for not only existing DNA analysis methods such as in-situ hybridization method, etc. but also a reagent for research of a telomere by applying PNA to a telomere PNA probe.

For example, the detection can be carried out by contacting a double strand DNA with a PNA having base sequence(s) complementary to all or a part of the base sequence of DNA and having been labeled with an organic EL-dye to hybridize, heating the mixture to form a single strand DNA, cooling slowly the mixture to room temperature to prepare a PNA-DNA conjugate, and measuring its fluorescence.

In the above-mentioned case, a method for measuring fluorescence of the product by amplifying the target nucleic acid by PCR method can be used. However, in this method, the amount of the amplified product should be measured by determining the size of the product by electrophoresis and measuring the fluorescence intensity. Alternatively, the amount of the product can be measured in real time using a probe that is designed to generate fluorescence by utilizing energy transfer of the fluorescence dye to hybridize with the product of the PCR method. For this method, for example, a DNA labeled with a donor and an acceptor can be used. Examples of specific detection method may include molecular beacon method in which the existence of a nucleic acid having a specific sequence is detected, TaqMan-PCR method, cycling probe method, etc.

For example, the luminescence mechanism of the molecular beacon method in which a molecular beacon is fixed on a substrate and hybridized with the object gene is explained with referring to FIG. 1. An organic EL-dye F is labeled on one end of a DNA (probe) having a specific DNA sequence and quencher Q is labeled on another end of the DNA. The quencher Q has been fixed on the substrate. Before the objective gene is introduced, the quencher Q and the organic EL-dye F are close to one another, and the fluorescence dye is quenched. When an object gene having a sequence complementary to the labeled DNA is introduced, the labeled DNA and the object gene are hybridized, whereby the distance between the organic EL-dye F and the quencher Q increases and the fluorescence of the organic EL-dye F can be observed. As a result, hybridization of DNA can be observed and the amount of hybridization can be measured.

Where the object to be detected is a protein, a chromatic dye is used for the detection of the protein after electrophoresis. Generally, a method comprising penetrating a chromatic dye such as Coomassie Brilliant Blue (CBB) to a gel after electrophoresis to stain a protein and irradiating the protein with UV to cause luminescence is used. Although such method using a conventional chromatic dye is convenient, it is not suitable for the detection of trace protein because the sensitivity is low as about 100 ng. Furthermore, the method also has a problem in that long time is required for dying because the chromatic dye is penetrated through the gel.

On the other hand, in the present invention, a protein is subjected to size separation by electrophoresis, and an organic EL-dye binds to the separated protein to label the protein. The organic EL-dye used for the present invention is suitable for the detection of trace protein, because it has a reactive group, reacts with a protein quickly and quantitatively and has high sensitivity. Furthermore, the protein separated by size separation can also be identified by mass analysis.

Examples of the protein that can be detected include simple proteins such as albumin, globulin, glutelin, histone, protamine, collagen, etc., and conjugated proteins such as nucleus protein, glycoprotein, riboprotein, phosphoprotein, metal protein, etc. For example, phosphoprotein, glycoprotein and whole protein can be stained in a protein sample separated by two-dimensional electrophoresis using three organic EL-dyes that correspond to chromatic dyes for phosphoprotein, glycoprotein and whole protein. Furthermore, since the protein can be identified by mass analysis such as TOF-Mass, etc., it can be applied to the diagnosis or treatment of diseases that produce specific protein such as cancer, infectious diseases due to virus, etc. Collagen is a protein that constitutes binding tissues of animals, and has a unique fibrous structure, i.e., a structure having three polypeptide strands in which said peptide strands aggregate to form a triple strand. Generally, collagen is a protein having quite low immunogenicity, and is widely used in the fields of foods, cosmetics, pharmaceuticals, etc. However, where a fluorescence dye is introduced in the peptide strand of collagen, its stability is insufficient where a conventional fluorescence dye is used. Therefore, a more stable fluorescence dye is required. Accordingly, stable and high sensitivity detection can be carried out by using an organic EL-dye as a fluorescence dye for labeling collagen.

Meanwhile, an aptamer can be used as a probe. Since the aptamer comprises an oligonucleic acid and can form various characteristic stereo structures depending on the base sequence, it can bind to many biomolecules including proteins via its stereo structure. Using this characteristic, the object substance can be detected by binding an aptamer labeled with an organic EL-dye to a specific protein, and detecting indirectly the object substance to be detected from the variation of fluorescence according to the change of the structure of the protein due to binding to the object substance to be detected. For example, a biosensor for detecting cocaine using an aptamer labeled with a fluorescence dye and utilizing energy transfer has been suggested (J. Am. Chem. Soc. 2001, 123, 4928-4931). By using an organic EL-dye instead of the above-mentioned fluorescence dye, a biosensor that provides high sensitivity and easy handling property can be provided.

Further, the labeling dye of the present invention can be used in the detection method of a biomolecule using a specific binding. That is, the method comprises of reacting a bonding material to be specifically bonded with the sample or bonding material to be specifically bonded with the modifier and a labeling dye comprising a coloring portion composing an organic EL-dye, a bonding portion to be bonded with a biomolecule and a spacer portion for linking the coloring portion and the bonding portion and measuring the fluorescence of the labeled biomolecule.

As for the combination of the sample or modifier and the binding material, such as antigen and antibody, hapten and anti-hapten antibody, biotin and avidin, Tag and anti-Tag antibody, lectin and glycoprotein, or hormone and receptor can be used.

Exemplarily, a specific binding property of antigen to antibody or hapten is utilized. That is, a specific antibody or hapten is detected by reacting a binding material such as antibody labeled with an organic EL-dye with antigen or hapten existing on substrate, in solution, on beads or on antibody. As antibody, protein, polysaccharide, nucleic acid or peptide can be used, and as hapten, low molecular weight molecule such as FITC or dintrophenyl group can be used. As the combination of antigen or hapten and antibody, GFP and anti-GFP antibody, or FITC and anti-FITC antibody can be listed.

As the exemplary method, the following methods can be used.
(1) A detection method comprising of binding an antibody labeled with a labeling dye to a biomolecule existing on substrate or in solution, wherein the biomolecule is antigen such as protein, polysaccharide, nucleic acid or peptide.
(2) A detection method comprising of binding an anti-hapten antibody labeled with a labeling dye to a biomolecule existing on substrate or in solution and modified with hapten, wherein the biomolecule is protein, polysaccharide, nucleic acid or peptide.
(3) A detection method comprising of binding avidin labeled with a labeling dye to a biomolecule existing on substrate or in solution and modified with biotin, wherein the biomolecule is protein, polysaccharide nucleic acid or peptide.
(4) A detection method comprising of binding an antibody to a biomolecule existing on substrate or in solution, and binding another antibody to the antibody which is labeled with a labeling dye and specifically binds to the antibody, wherein the biomolecule is protein, polysaccharide, nucleic acid or peptide.
(5) A detection method comprising of binding an antibody labeled with hapten to a biomolecule existing on substrate or in solution, and binding another antibody to hapten which is labeled with a labeling dye and specifically binds to hapten, wherein the biomolecule is protein, polysaccharide or nucleic acid.
(6) A detection method comprising of binding an antibody labeled with biotin to a biomolecule existing on substrate or in solution, and binding avidin to biotin which is labeled with a labeling dye and specifically binds to biotin, wherein the biomolecule is protein, polysaccharide or nucleic acid.
(7) A detection method comprising of binding Tag such as histidine to a biomolecule existing on substrate or in solution, and binding anti-Tag antibody labeled with a labeling dye to Tag, wherein the biomolecule is protein, polysaccharide or nucleic acid.

These labeled materials can be used in various measuring method such as Immunostaining, ELISA, Western blotting or Flow cytometry.

Figure 2:
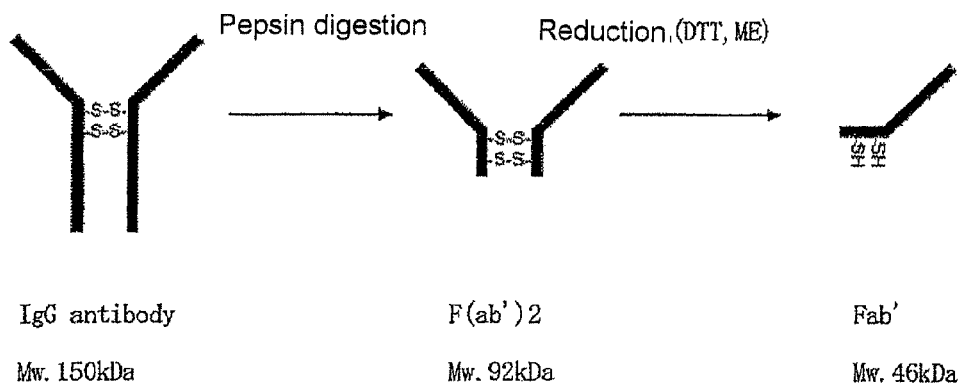
FIG. 2 is a schematic diagram showing a preparation method of F(ab') fragment of an InG antibody in a detection method of the present invention.
Figure 3:
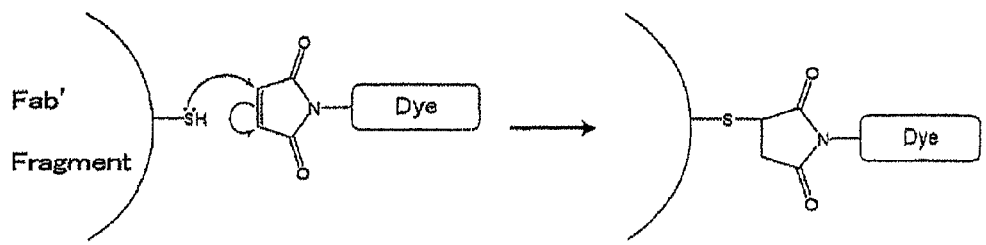
FIG. 3 is a schematic diagram showing a method for introducing an organic EL-dye to F(ab') fragment of an InG antibody in a detection method of the present invention.

Further, for example, as shown in FIG. 2, a fragment that referred to as F (ab')$_2$ can be obtained by treating an IgG antibody with pepsin. The fragment is reduced using dithiothreitol, etc. to give a fragment that referred to as Fab'. The Fab' fragment has one or two thiol group(s) (—SH). Specific reaction can be carried out by reacting the thiol group(s) with maleimide group(s). Namely, as shown in FIG. 3, an antibody can be labeled with an organic EL-dye by reacting the organic EL-dye in which maleimide group(s) have been introduced with thiol group(s) of a fragment. In this case, the physiological activity (antibody capturing ability) of the antibody is not deteriorated.

Alternatively, metal ion can be detected using the detection method of the present invention. Metal ion participates to every life phenomena that occur in a living body, such as maintenance of stability and high dimension structure of DNAs, proteins, etc. in a body, expression of functions, activation of enzymes that control all chemical reactions in a living body, etc. Therefore, importance of a metal ion sensor, which can observe behavior of metal ion in a living body in real time, is growing in the field of medical. Conventionally, a metal ion sensor in which a fluorescence dye has been introduced in a biomolecule is known. For example, a metal ion sensor that utilizes a nucleic acid having a sequence that forms a specific structure by incorporating $K^+$ ion in the presence of $K^+$ ion has been suggested (J. AM. CHEM. SOC. 2002, 124, 14286-14287). A fluorescence dye that initiates energy transfer is introduced in both ends of a nucleic acid. Generally, energy transfer does not occur due to distance between the dyes. However, in the presence of $K^+$ ion, the nucleic acid forms a specific shape, whereby the fluorescence dyes verge in a distance that occurs energy transfer and fluorescence can be observed. In addition, a zinc ion sensor in which a fluorescence dye has been introduced in a peptide has been suggested (J. Am. Chem. Soc. 1996, 118, 3053-3054). By using a label dye comprising an organic EL-dye of the present invention instead of these conventional fluorescence dyes, a metal ion sensor that provides high sensitivity and easy handling property can be provided. All kinds of metal ion existing in a living body can be detected.

Moreover, intercellular signal can be observed using the detection method of the present invention. For the response of cells to internal signal or environmental information, various molecules from ions to enzymes are participated. It is known that in the process of signal transmission, a specific protein kinase is activated and induces phosphoration of a specific cell protein, which bears initial response for various cell responses. Binding and hydrolysis of nucleotides play an important role in these activities, and signal transmission behavior can be readily observed using a nucleotide derivative. For example, protein kinase C (PKC) plays an important role for signal transmission in a cell membrane. This $Ca^{2+}$ dependant serine/threonine protein kinase is activated on a membrane-constituting lipid such as diacylglycerol, phosphatidyl serine, etc., which phosphorizes serine and threonine existing on an ion channel and a cell skeleton protein to vary electron charge on the membrane surface, whereby signal transmission is achieved. By dynamically observing these phenomena in living cells, signal transmission of the cells can be observed.

In this observation, the nucleotide derivative is provided as a substrate or an inhibitor for an enzyme, and it is used for search for the structure and dynamics of a lone protein and reconstruction of a membrane binding protein enzyme, and binds to organelle such as mitochondria, nucleotide-binding protein portion of tissues such as skinned muscle fiber so as to control them. Furthermore, existence of compounds that affect signal transmission such as inhibitors or active forms for G-protein has been recently revealed. By introducing the labeled dye including the organic EL-dye of the present invention into this nucleotide derivative, dynamic observation of the intercellular signal transmission thereof can be carried out at high sensitivity and with easy handling.

Alternatively, the detection method of the present invention can be used for the observation of gene expression utilizing RNA interference (RNAi). RNAi is a phenomenon where RNA is introduced into a cell, the expression of gene having the same sequence as said RNA is knocked down. The RNAi decompose mRNA of the target gene by introducing a double strand RNA (dsRNA) into a cell and suppresses expression. In this process, a long chain dsRNA (double stranded RNA) is firstly cleaved into a short chain siRNAs having 21 to 23 mers by Dicer having ribonuclease activity. It is known that the generated siRNAs are uptaken by an intermediate conjugate (RNA-induced silencing complex (RISC)), whereby mRNAs having sequences complementary to the antisense chains of the siRNAs uptaken by this conjugate are cleaved. Also in this field, a fluorescence dye is used for observing gene expression state, etc. Using an organic EL-dye as a fluorescence dye for labeling, stable and high sensitivity detection can be carried out.

The labeled dye of the present invention can also be used as a chromatic dye for tissues or cells used for determination of the expression level of the target nucleic acid or target protein in a tissue sample or a cell sample. The tissues or cells can be stained by binding an organic EL-dye with a target nucleic acid or a target protein via reactive groups as mentioned above.

Accordingly, the chromatic dye of the present invention shows superior performance than conventional dyes in view of storage after labeling, since the organic EL-dye generates fluorescence even in dry state when it is used, for example, for staining of eucaryotic cells. Furthermore, it can also be sufficiently used as a dye for cell skeletons as well as a dye for eucaryotic cells. Moreover, it can be used for labeling of mitochondria, Golgi body, endoplasmic reticulumlysosome, lipid double membrane, etc. These labeled cells, etc. can be observed under all wet or dry conditions, and thus have great versatility. A fluorescence microscope, etc. can be used for observation.

Generally, tissues collected from human bodies during clinical stage are sliced using an instrument such as a microtome, etc. in thin slices and stained. In this case, Cy dye and Alexa dye are used. However, since the existing dyes have poor stability, it is necessary to prepare samples again in the next diagnosis. Furthermore, the samples prepared cannot be stored in the form of a specimen. On the other hand, the organic EL-dye is a very stable dye as compared to the above-mentioned conventional dyes. Therefore, the stained tissues can be stored in the form of a specimen.

A labeling kit of the present invention contains a labeling dye comprising a coloring portion composing an organic EL-dye, a bonding portion to be bonded with a biomolecule and a spacer portion for linking the coloring portion and the bonding portion, and if necessary, it can contain reagents, enzymes, solvents, etc., for reacting a dye with the object biomolecule. The object biomolecules include nucleic acids, proteins, peptides or saccharides.

Another labeling kit of the present invention contains at least a labeling dye precursor comprising a coloring portion composing an organic EL-dye and spacer portion to be bonded with the a coloring portion and represented by the before mentioned general formula (I), and if necessary, it can contain a reagent for introducing any one reactive group selected from a group consisting of a carboxylic acid group, an isocyanate group, an isothiocyanate group, an epoxy group, a halogenated alkyl group, a triazine group, a carbodiimide group and an active-esterified carbonyl group.

The present invention will be further specifically explained in more detail in the following examples.

Synthesis Example 1

A 1,2,5-oxadiazolo-[3,4-c]pyridine derivative was used as the organic EL-dye.

The scheme for synthesis of an active ester of a 1,2,5-oxadiazolo-[3,4-c]pyridine in which —COO— is introduced as a spacer portion will be shown below (scheme 2 and 3). Here, hereinafter, the active ester having no spacer portion is abbreviated as EL-OSu, and the active ester in which the spacer portion is introduced is abbreviated as EL-OSu-Sp.

Scheme 2.

Formula 33

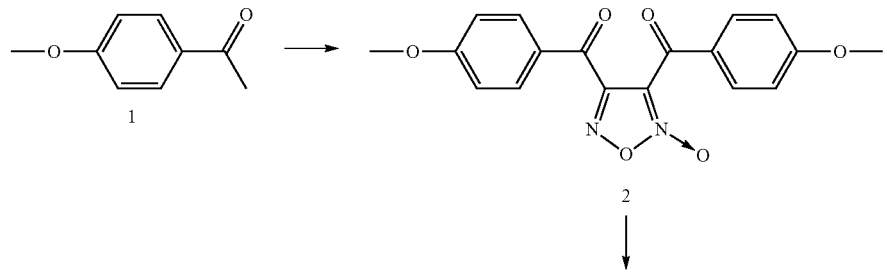

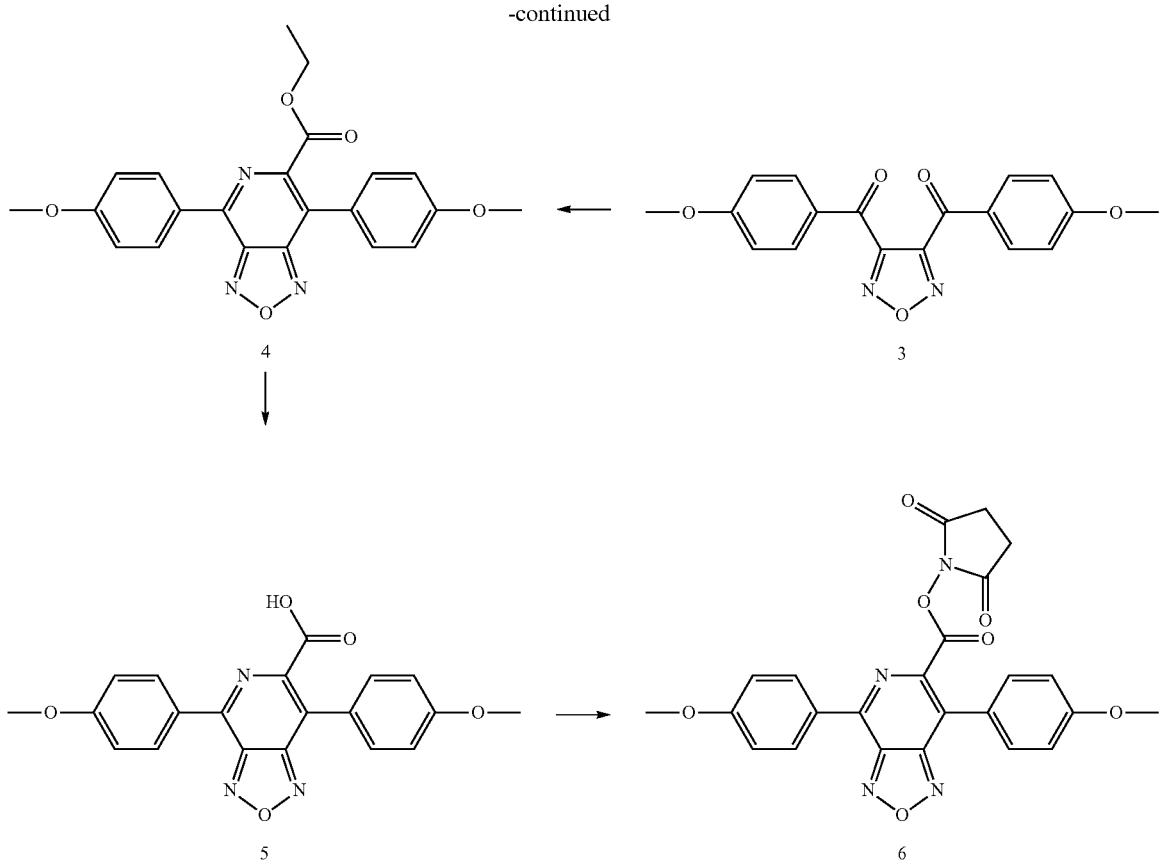
Next, an active ester of oxadiazolopyridine (6) was reacted with alanine in DMF to obtain carboxylic acid (7). Then, carboxylic acid (7) was reacted with N-hydroxysuccinimide in dioxane to obtain an active ester of oxadiazolopyridine (7) in which the spacer portion is introduced. The following scheme shows a reaction example.
Scheme 3.
Formula 34
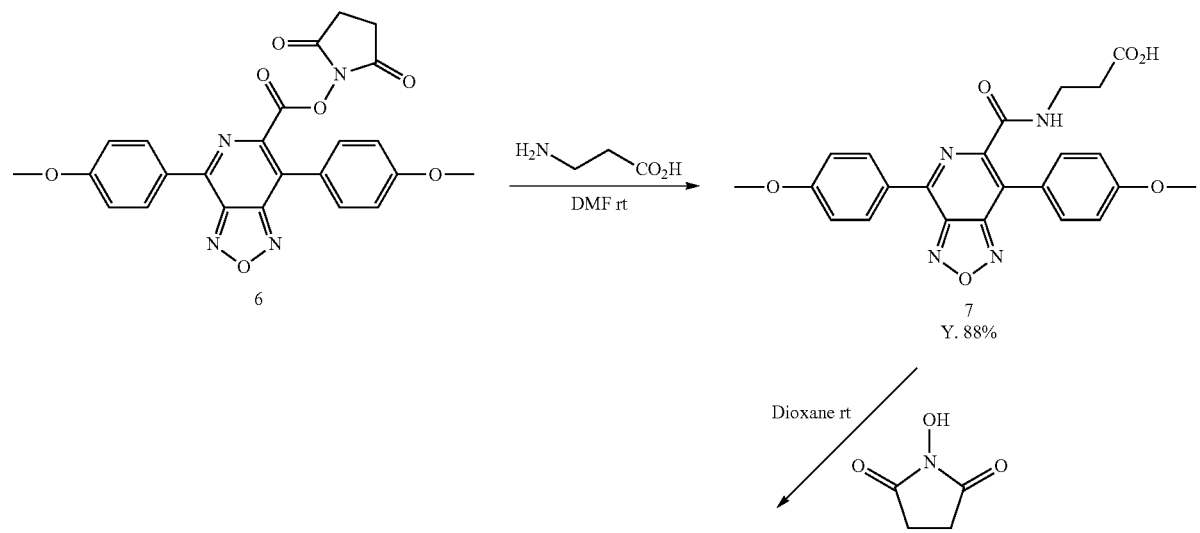

-continued

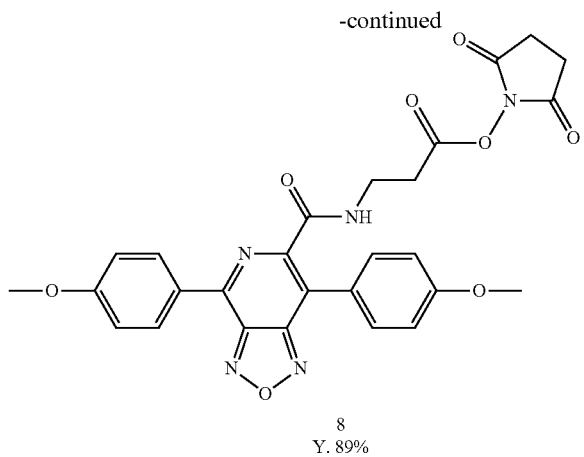

8
Y. 89%

In each step, the reaction mildly proceeded and the objective active ester (8) was obtained via carboxylic acid (7) in high yield.

(Synthetic Step)
(1) Synthesis of Diketone Derivative (2)

In a 500 ml three-necked flask, 37.5 g (0.25 mol) of 4-methoxyacetophenone (1) and 0.15 g of sodium nitrite were dissolved in 100 ml of acetic acid. On a water bath, a solution prepared by dissolving 100 ml of $HNO_3$ in 100 ml of acetic acid was added dropwise over 2 hours. Then, the mixture was stirred at room temperature for 2 days. The reaction mixture was slowly added into 500 ml of water to cause precipitation. The precipitate was filtrated and dissolved in chloroform. The chloroform phase was washed with saturated sodium bicarbonate water, and washed twice with a 10% NaCl aqueous solution. After dehydration over $MgSO_4$, chloroform was distilled off under reduced pressure to obtain 34.5 g (yield: 78%) of oxadiazole-N-oxide (2).

(2) Synthesis of Diketone Derivative (3)

In a 500 ml three-necked flask, 17.7 g (0.05 mol) of oxadiazole-N-oxide (2) was dissolved in 400 ml of acetonitrile. Into this was added 12.0 g of Zn, 7 ml of AcOH and 20 ml of $Ac_2O$. On a water bath, the resulted mixture was cooled so that the reaction temperature did not exceed 30° C. The mixture was stirred for 12 hours to terminate the reaction. The reaction mixture was filtrated to remove insoluble materials. Acetonitrile was distilled off under reduced pressure to obtain a residue. The residue was recrystallized from chloroform to obtain 10.2 g (yield: 60%) of oxadiazole-N-oxide (3).

(3) Synthesis of Oxadiazolopyridine Ethyl Ester (4)

In a 500 ml three-necked flask, 15.6 g (0.046 mol) of oxadiazole-N-oxide (3) was dissolved in 300 ml of butanol. Into this was added 32.0 g (0.23 mol) of a glycine ethyl ester hydrochloride. The mixture was heated to reflux for 24 hours Butanol was distilled off under reduced pressure to obtain a residue. The residue was dissolved in 200 ml of chloroform, and washed with 10% HCl, saturated $NaHCO_3$ and 10% NaCl. This was dried over $MgSO_4$ and the solvent was distilled off. The resulted residue was recrystallized from chloroform to obtain 13.0 g (yield: 70%) of oxadiazolopyridine ethyl ester (4).

(4) Hydrolysis of Oxadiazolopyridine Ethyl Ester (4)

In a 500 ml three-necked flask, 3.0 g (0.007 mol) of oxadiazolopyridine ethyl ester (4) was dissolved in 200 ml of ethanol. To this was added 0.62 g (0.01 mol) of KOH. After heating to reflux for 5 hours, the reaction mixture was added to 200 ml of water. Into this aqueous solution, concentrated hydrochloric acid was added dropwise to adjust pH to 1 to obtain a precipitate. The precipitate was filtrated and dissolved in chloroform. The chloroform phase was washed with a 10% $NaHCO_3$ aqueous solution and water. Chloroform was distilled off to obtain a residue. The residue was recrystallized from water-ethanol (1:1) to obtain 2.1 g (yield: 81%) of oxadiazolopyridinecarboxylic acid (5)

(5) Synthesis of Active Ester (6)

In a 50 ml three-necked flask, 1.0 g (0.0026 mol) of oxadiazolopyridinecarboxylic acid (5) and 0.30 g (0.0026 mol) of N-hydroxysuccinimide were dissolved in 20 ml of DMF. Into this, 0.54 g (0.0026 mol) of N,N'-dicyclohexylcarbodiimide was added dropwise over 30 minutes. After dropping, the mixture was stirred for 30 hours at room temperature. Under reduced pressure, DMF was distilled off. The residue was isolated and purified by silica gel column chromatography (chloroform) to obtain 0.76 g (yield: 62%) of an oxadiazolopyridine active ester (6).

(6) Synthesis of Carboxylic Acid (7)

In a 50 ml three-necked flask, 100 mg (0.21 mmol) of oxadiazolopyridinecarboxylic acid (5) and 18.8 mg (0.21 mmol) of alanine were dissolved in 20 ml of DMF. After dropping, the mixture was stirred for 12 hours at room temperature. Under reduced pressure, DMF was distilled off. The residue was isolated and purified by silica gel column chromatography (chloroform:methanol=7:3) to obtain 83 mg (yield: 88%) of a carboxylic acid (7).

(7) Synthesis of Active Ester (8)

In a 50 ml three-necked flask, 70 mg (0.16 mmol) of oxadiazolopyridinecarboxylic acid (7) and 18.0 mg (0.16 mmol) of N-hydroxysuccinimide were dissolved in 20 ml of DMF. Into this, 32.2 mg (0.16 mmol) of N,N'-dicyclohexylcarbodiimide dissolved in 5 ml of DMF was added dropwise over 30 minutes. After dropping, the mixture was stirred for 30 hours at room temperature. Under reduced pressure, DMF was distilled off. The residue was isolated and purified by silica gel column chromatography (chloroform) to obtain 75:8 mg (yield: 89%) of an active ester (8).

Synthesis Example 2

An imidazolopyridine ethyl ester derivative was used as an organic EL-dye.

The scheme for synthesis of an active ester of imidazolopyridine ethyl ester in which —COO— is introduced as a spacer portion will be shown below (scheme 4 and 5).

Scheme 4.

Formula 35

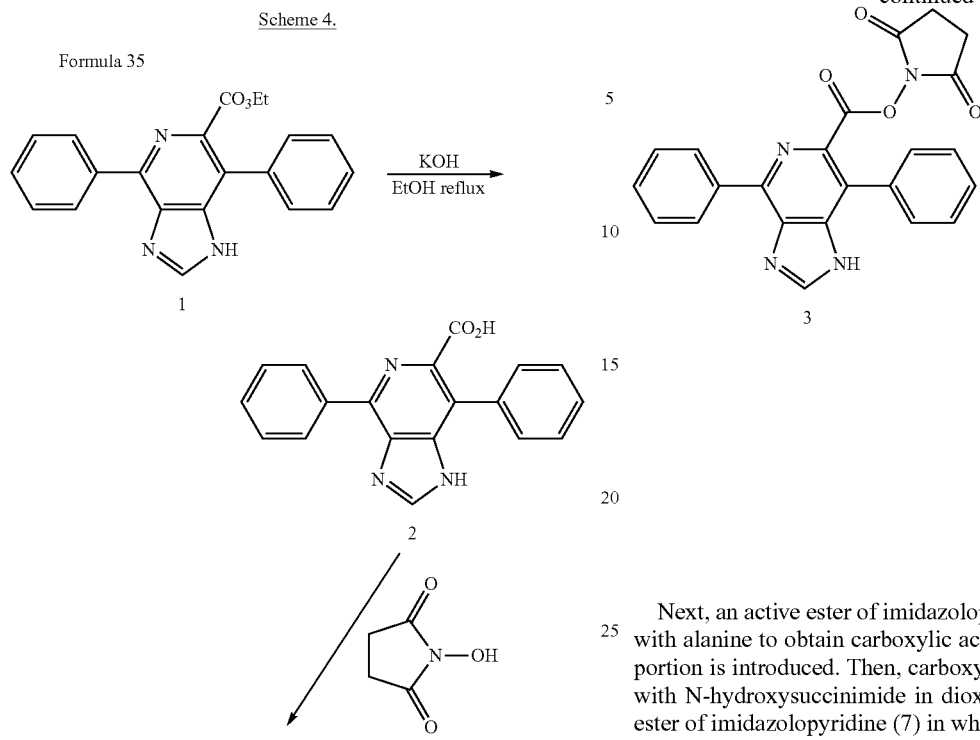

Next, an active ester of imidazolopyridine (3) was reacted with alanine to obtain carboxylic acid (4) in which a spacer portion is introduced. Then, carboxylic acid (4) was reacted with N-hydroxysuccinimide in dioxane to obtain an active ester of imidazolopyridine (7) in which the spacer portion is introduced. The following scheme shows a reaction example.

Scheme 5.

Formula 36

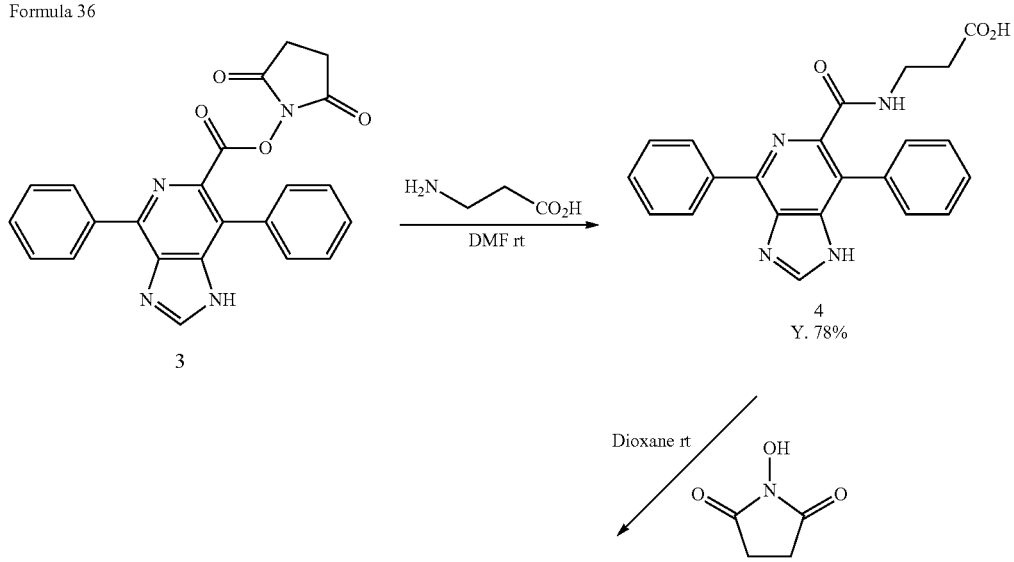

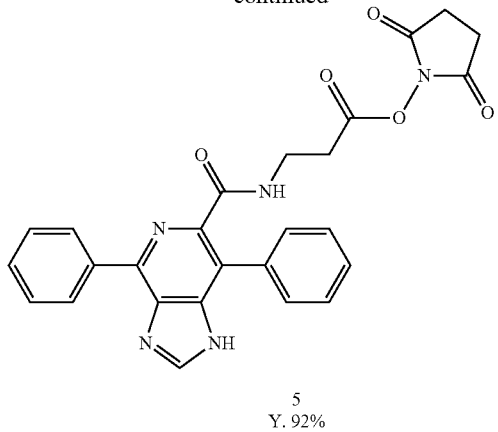

5
Y. 92%

(1) Hydrolysis of Imidazolopyridine Ethyl Ester (1)

In a 500 ml three-necked flask, 0.5 g (1.5 mmol) of an ester 1 was dissolved in 50 ml of ethanol. To this was added 0.12 g (2.1 mol) of KOH. After heating to reflux for 5 hours, the reaction mixture was added to 50 ml of water. Into this aqueous solution, concentrated hydrochloric acid was added dropwise to adjust pH to 1 to obtain a precipitate. The precipitate was filtrated and dissolved in chloroform. The chloroform phase was washed with a 10% NaHCO$_3$ aqueous solution and water. Chloroform was distilled off to obtain a residue. The residue was recrystallized from water to obtain 0.3 g (yield: 63%) of a carboxylic acid 2.

(2) Synthesis of Active Ester (3)

In a 50 ml three-necked flask, 0.2 g (0.6 mmol) of a carboxylic acid derivative 2 and 0.07 g (0.6 mmol) of N-hydroxysuccinimide were dissolved in 10 ml of DMF. Into this, 0.12 g (0.6 mmol) of N,N'-dicyclohexylcarbodiimide was added dropwise over 30 minutes. After dropping, the mixture was stirred for 30 hours at room temperature. Under reduced pressure, DMF was distilled off. The residue was isolated and purified by silica gel column chromatography (chloroform) to obtain 0.14 g (yield: 55%) of an active ester 3.

(3) Synthesis of carboxylic acid (4)

In a 50 ml three-necked flask, 80 mg (0.19 mmol) of an active ester of imidazolopyridine (5) and 17.3 mg (0.19 mmol) of alanine were dissolved in 20 ml of DMF. After dropping, the mixture was stirred for 10 hours at room temperature. Under reduced pressure, DMF was distilled off. The residue was isolated and purified by silica gel column chromatography (chloroform:methanol=7:3) to obtain 58 mg (yield: 78%) of a carboxylic acid (4).

(4) Synthesis of Active Ester (5)

In a 50 ml three-necked flask, 54 mg (0.14 mmol) of imidazolopyridine carboxylic acid (4) and 16.1 mg (0.14 mmol) of N-hydroxysuccinimide were dissolved in 20 ml of DMF. Into this, 28.8 mg (0.14 mmol) of N,N'-dicyclohexylcarbodiimide dissolved in 5 ml of DMF was added dropwise over 30 minutes. After dropping, the mixture was stirred for 30 hours at room temperature. Under reduced pressure, DMF was distilled off. The residue was isolated and purified by silica gel column chromatography (chloroform) to obtain 62.2 mg (yield: 92%) of an active ester (5).

Synthesis Example 3

An oxadiazolopyridine derivative used in Synthesis Example 1 was used as an organic EL-dye, and cysteic acid was used as a spacer portion, and both of an active esterified carbonyl group and sulfonium group of anionic group were introduced as a reactive group. An active ester of oxadiazolopyridine (6) was reacted with cysteic acid to obtain carboxylic acid (9) in which the spacer portion is introduced.

Next, carboxylic acid (9) was reacted with N-hydroxysuccinimide in dioxane to obtain an active ester of oxadiazolopyridine (10) in which the spacer portion is introduced. The following scheme shows a reaction example.

Scheme 6.

Formula 37

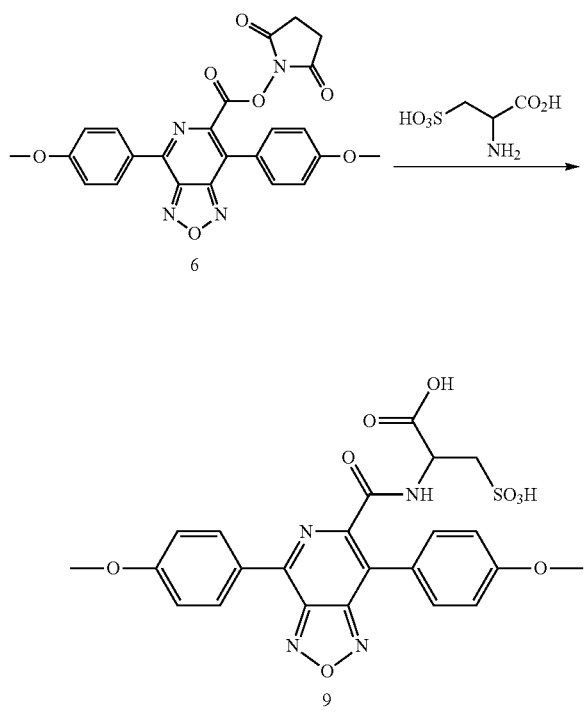

-continued

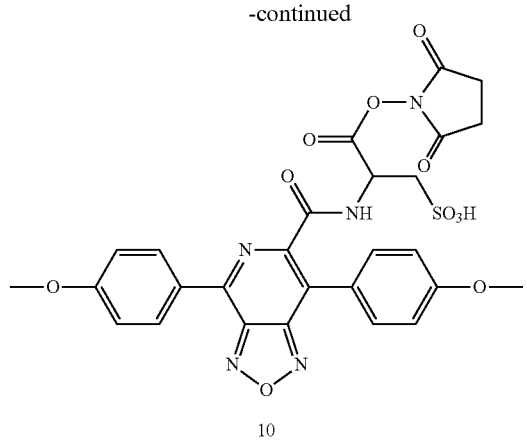

10

The following shows reaction steps which are different from Synthesis Example 1.
(1) Synthesis of Carboxylic Acid (9)

In a 50 ml three-necked flask, 100 mg (0.21 mmol) of an oxadiazolopyridine carboxylic acid (9) and 39 mg (0.23 mmol) of cysteic acid were dissolved in 20 ml of DMF. After dropping, the mixture was stirred for 12 hours at room temperature. Under reduced pressure, DMF was distilled off. The residue was isolated and purified by silica gel column chromatography (chloroform:methanol=7:3) to obtain 98 mg (yield: 88%) of a carboxylic acid (9).
(2) Synthesis of Active Ester (10)

In a 50 ml three-necked flask, 80 mg (0.15 mmol) of oxadiazolopyridine carboxylic acid (9) and 19 mg (0.17 mmol) of N-hydroxysuccinimide were dissolved in 20 ml of DMF. Into this, 35 mg (0.17 mmol) of N,N'-dicyclohexylcarbodiimide dissolved in 5 ml of DMF was added oxadiazolopyridine dropwise over 30 minutes. After dropping, the mixture was stirred for 30 hours at room temperature. Under reduced pressure, DMF was distilled off. The residue was isolated and purified by silica gel column chromatography (chloroform:methanol=10:1) to obtain 73 mg (yield: 78%) of an active ester (10).

Synthesis Example 4

An oxadiazolopyridine derivative used in Synthesis Example 1 was used as an organic EL-dye, and serine was used as a spacer portion. An active ester of oxadiazolopyridine (6) was reacted with serine to obtain carboxylic acid (11) in which the spacer portion is introduced. Next, carboxylic acid (11) was reacted with N-hydroxysuccinimide in dioxane to obtain an active ester of oxadiazolopyridine (12) in which the spacer portion is introduced. The following scheme shows a reaction example.

Scheme 7.

Formula 38

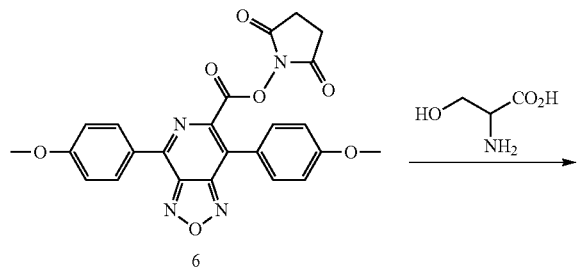

6

-continued

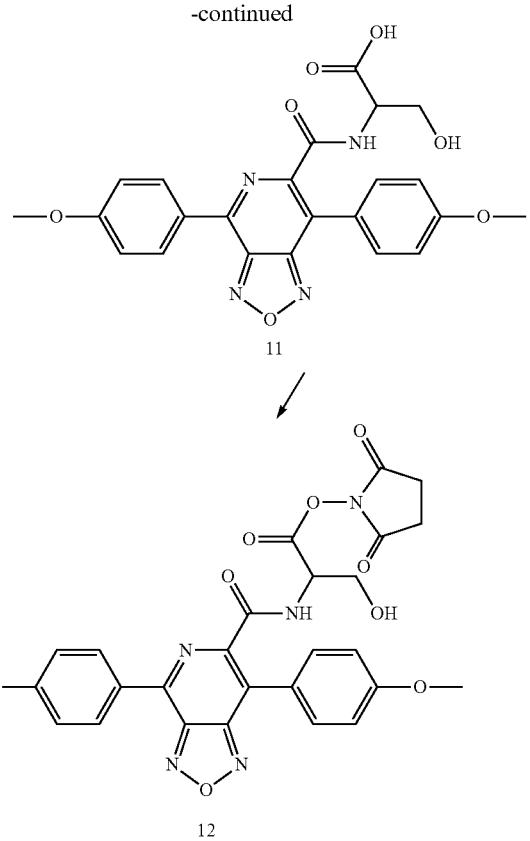

11

12

The following shows reaction steps which are different from Synthesis Example 1.
(1) Synthesis of Carboxylic Acid (11)

In a 50 ml three-necked flask, 100 mg (0.21 mmol) of an oxadiazolopyridine carboxylic acid (9) and 26 mg (0.25 mmol) of serine were dissolved in 20 ml of DMF. After dropping, the mixture was stirred for 12 hours at room temperature. Under reduced pressure, DMF was distilled off. The residue was isolated and purified by silica gel column chromatography (chloroform:methanol=7:3) to obtain 79 mg (yield: 81%) of a carboxylic acid (11).
(2) Synthesis of Active Ester (12)

In a 50 ml three-necked flask, 70 mg (0.15 mmol) of oxadiazolopyridine carboxylic acid (9) and 19 mg (0.17 mmol) of N-hydroxysuccinimide were dissolved in 20 ml of DMF. Into this, 35 mg (0.17 mmol) of N,N'-dicyclohexylcarbodiimide dissolved in 5 ml of DMF was added oxadiazolopyridine dropwise over 30 minutes. After dropping, the mixture was stirred for 30 hours at room temperature. Under reduced pressure, DMF was distilled off. The residue was isolated and purified by silica gel column chromatography (chloroform:methanol=10:1) to obtain 61 mg (yield: 72%) of an active ester (12).

Synthesis Example 5

An oxadiazolopyridine derivative used in Synthesis Example 1 was used as an organic EL-dye, and alanylserine (Ala-Ser) of a peptide linker was used as a spacer portion. An active ester of oxadiazolopyridine (6) was reacted with alanylserine to obtain carboxylic acid (13) in which the spacer portion is introduced. Next, carboxylic acid (13) was reacted with N-hydroxysuccinimide in dioxane to obtain an active ester of oxadiazolopyridine (14) in which the spacer portion is introduced. The following scheme shows a reaction example.

Scheme 8.

Formula 39

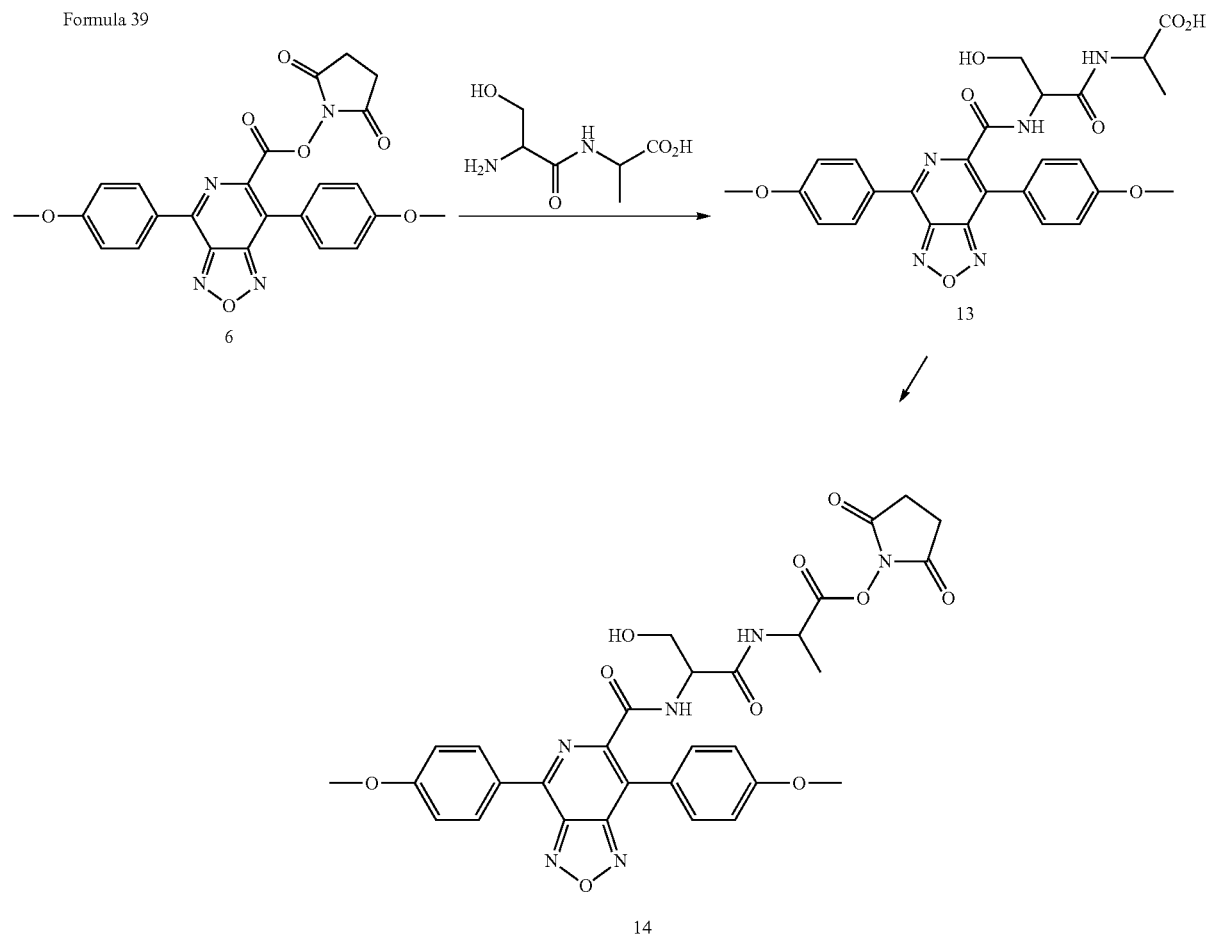

The following shows reaction steps which are different from Synthesis Example 1.

(1) Synthesis of Carboxylic Acid (13)

In a 50 ml three-necked flask, 100 mg (0.21 mmol) of an oxadiazolopyridine carboxylic acid (9) and 45 mg (0.25 mmol) of alanylserine were dissolved in 20 ml of DMF. After dropping, the mixture was stirred for 10 hours at room temperature. Under reduced pressure, DMF was distilled off. The residue was isolated and purified by silica gel column chromatography (chloroform:methanol=6:4) to obtain 72 mg (yield: 64%) of a carboxylic acid (13).

(2) Synthesis of Active Ester (14)

In a 50 ml three-necked flask, 60 mg (0.11 mmol) of oxadiazolopyridine carboxylic acid (13) and 14 mg (0.12 mmol) of N-hydroxysuccinimide were dissolved in 15 ml of DMF. Into this, 25 mg (0.12 mmol) of N,N'-dicyclohexylcarbodiimide dissolved in 5 ml of DMF was added oxadiazolopyridine dropwise over 30 minutes. After dropping, the mixture was stirred for 15 hours at room temperature. Under reduced pressure, DMF was distilled off. The residue was isolated and purified by silica gel column chromatography (chloroform:methanol=8:2) to obtain 60 mg (yield: 86%) of an active ester (14).

Synthesis Example 6

An oxadiazolopyridine derivative used in Synthesis Example 1 was used as an organic EL-dye, and ethylene glycol acid was used as a spacer portion. The following scheme shows a reaction example.

Scheme 9.

Formula 40

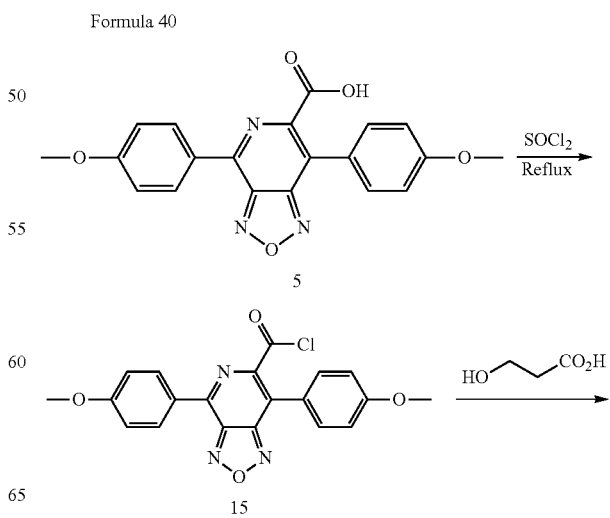

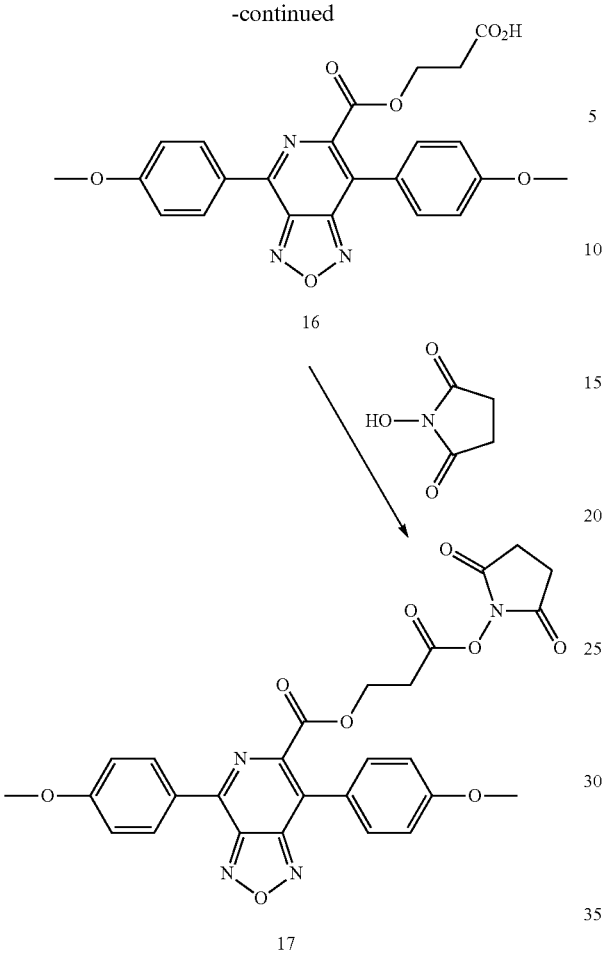

(1) Synthesis of Acid Chloride (15)

In a 50 ml three-necked flask, 100 mg (0.27 mmol) of an oxadiazolopyridine carboxylic acid (5) was mixed with 20 ml of $SOCl_2$, and the mixture was refluxed for 2 hours. After cooling to room temperature, $SOCl_2$ was distilled off to obtain 94 mg (yield: 90%) of an acid chloride (15).

(2) Synthesis of Carboxylic Acid (16)

In a 50 ml three-necked flask, 90 mg (0.22 mmol) of an oxadiazolopyridine acid chloride (15) was mixed with 40 ml of THF. Into this, 20 mg (0.22 mmol) of ethylene glycol acid dissolved in 5 ml of DMF was added, and the mixture was stirred for 1 hour. Then THF was distilled off. The residue was recrystallized in methanol to obtain 61 mg (yield: 61%) of a carboxylic acid (16).

(3) Synthesis of Active Ester (17)

In a 50 ml three-necked flask, 100 mg (0.22 mmol) of oxadiazolopyridine carboxylic acid (16) and 29 mg (0.24 mmol) of N-hydroxysuccinimide were dissolved in 25 ml of DMF. Into this, 50 mg (0.24 mmol) of N,N'-dicyclohexylcarbodiimide dissolved in 10 ml of DMF was added oxadiazolopyridine dropwise over 30 minutes. After dropping, the mixture was stirred for 15 hours at room temperature. Under reduced pressure, DMF was distilled off. The residue was isolated and purified by silica gel column chromatography (chloroform:methanol=7:3) to obtain 107 mg (yield: 89%) of an active ester (17).

Synthesis Example 7

An active ester of oxadiazolopyridine (6) of Synthesis Example 3 was synthesized by using an oxadiazolopyridine derivative used in Synthesis Example 1 as an organic EL-dye and taurine as a spacer portion.

In a 100 ml of recovery flask, 0.48 g (1.08 mmol) of an active ester of oxadiazolopyridine (15), 0.52 g of an impurity such as DCC and 0.43 g (3.44 mmol) of taurine (molecular weight:125.15) were introduced, and furthermore, 50 ml of anhydrous DMF was added. Into this, 715 μL (514 mmol) of triethylamine (TEA, molecular weight:101.19, 1 L ☐0.73 kg) was added, and the mixture was stirred for 4 hours. The reaction was confirmed to have ended in 2 hours by TLC (in case of using chloroform:methanol=6:4, Rf of raw material is 0.89 and Rf of objectives is 0.69, and in case of using chloroform:methanol=7:3, Rf of raw material is 0.89 and Rf of objectives is 0.49).

Under reduced pressure, DMF was distilled off. The residue was isolated and purified by silica gel column chromatography (chloroform:methanol=3:1) to dispense the objective. As a crystal formation was observed in the dispensed solution, the crystal was separated by filtration. The crystal was confirmed to be an objective by HPLC (see FIG. 3) and TLC. The amount of the objective was 238 mg (yield: 58%).

Example 1

Labeling of Oligonucleotide with Dye, and Detection Thereof (1)

(Oligonucleotide)

The followings are used oligo-DNA.

```
17 mer DNA
H2N-(C6)-5'-ACT CCA GTG GTA ATC TA-3'

20 mer DNA
H2N-(C6)-5'-ACT CCA GTG GTA ATC TAC TG-3'

40 mer DNA
H2N-(C6)-5'-ACT CCA GTG GTA ATC TAC TGG
GAC GAC GGA ACA GCT TTG AGG T-3'
```

(Labeling Procedure)

An active ester of oxadiazolopyridine (8) (EL-OSu-Sp) synthesized in Synthesis Example 1 was used as a labeling dye. An example of 20 mer oligonucleotide as oligo-DNA is explained.

Into 20 μl of borate buffer (pH 8.5) containing $H_2N$—(C6)-5'-ACT CCA GTG GTA ATC TAC TG-3 (10 nmol) was added 80 μl of an anhydrous DMSO solution containing 12 nmol (5.7 μg) (1.2 equivalent) of an active ester of an organic EL-dye (EL-OSu-Sp) and the mixture was shaken at room temperature for 6 hours. After shaking, 0.1 M TEAA (triethylamine acetic acid) buffer (pH 7.0) was added so as to give the total volume of 1 ml, and components derived from the oligonucleotide were separated using NAP-10 column (GE Healthcare Sephadex G-25). In this operation, the NAP-10 column had been equilibrated previously with 15 ml of 0.1 M TEAA buffer before use. The sample solution of which total volume had been adjusted to 1 ml was applied into in a column. After elution of 1 ml of the solution, 0.1 M TEAA buffer was charged in a volume of 1.5 ml. Immediately after this, 1.5 ml of the eluted solution was separated. 100 μl of the resulted solution was analyzed by reverse phase HPLC.

For comparison, an active ester of oxadiazolopyridine (EL-OSu) having no spacer portion was used as a labeling dye for oligo-DNA. An active ester of Alexa 594 of Molecular Probe Corporation was also used for a part of comparison.

The incorporation ratio was obtained by comparing the peak area of HPLC spectra.

(HPLC Measurement Conditions)

As a HPLC apparatus, LC-2000 plus series of JASCO Corporation was used.

Column: GL Science Inertsil ODS-3 Column 5 μm, 4.6 mm×250 mm

Gradient conditions of HPLC measurement

Eluent solvent A: 0.1 M TEAA solution (pH 7.0)

Eluent solvent B: 90% CH$_3$CN/0.1 M TEAA solution (pH 7.0)

Gradient (B %) 0 min (10%)->30 min (45%)->40 min (100%)->50 min (100%)->60 min (10%)

Flow rate: 1 ml/min

Temperature: 40° C.

(Result)

Figure 4A:
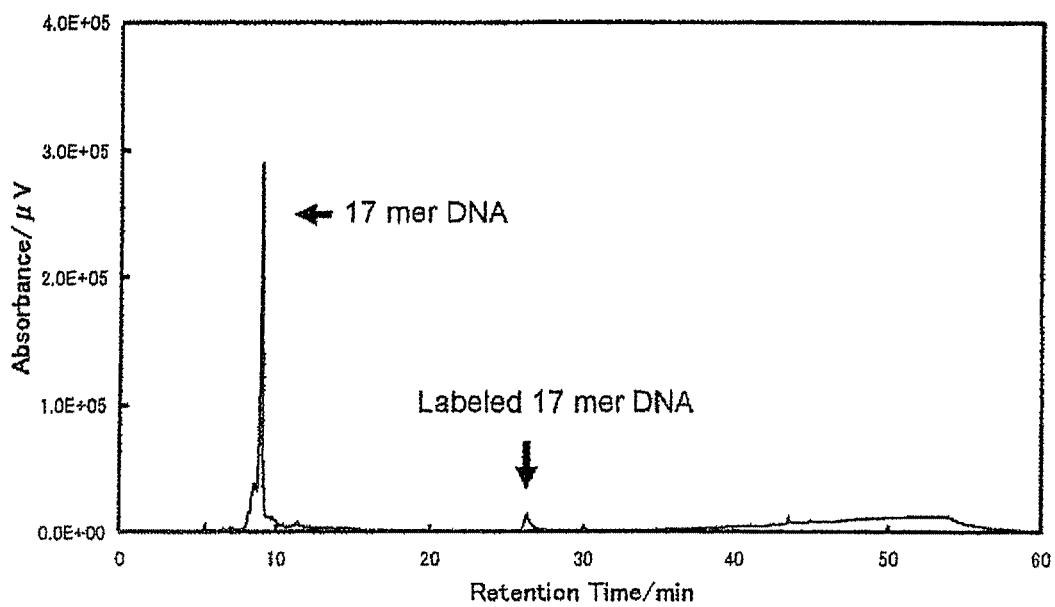
FIG. 4A shows one example of the HPLC profile of a labeled 17 mer DNA with EL-OSu in Example 1 of the present invention.
Figure 4B:
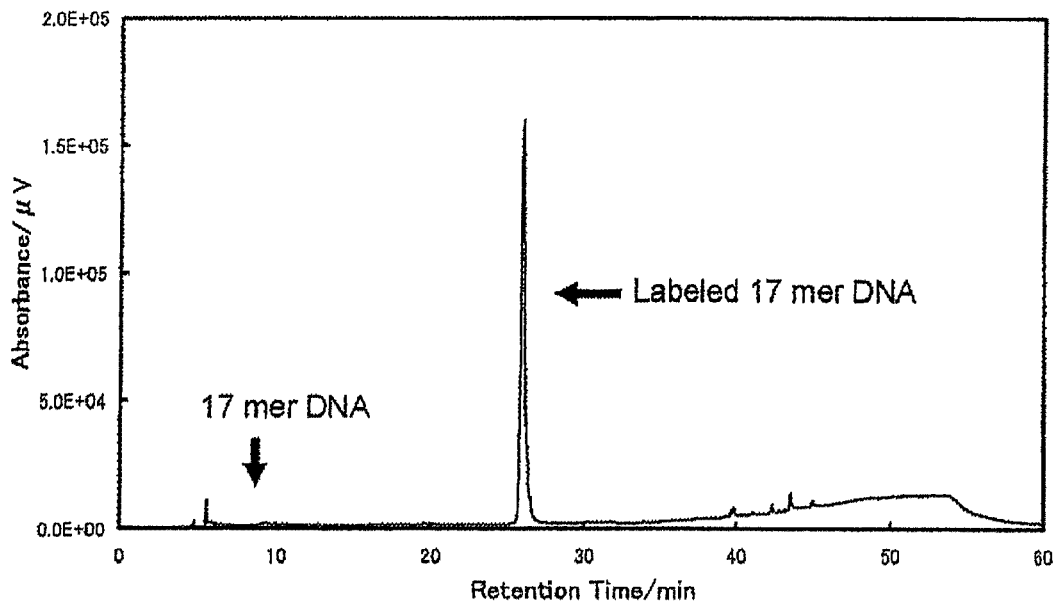
FIG. 4B shows one example of the HPLC profile of a labeled 17 mer DNA with EL-OSu-Sp in Example 1 of the present invention.
Figure 5A:
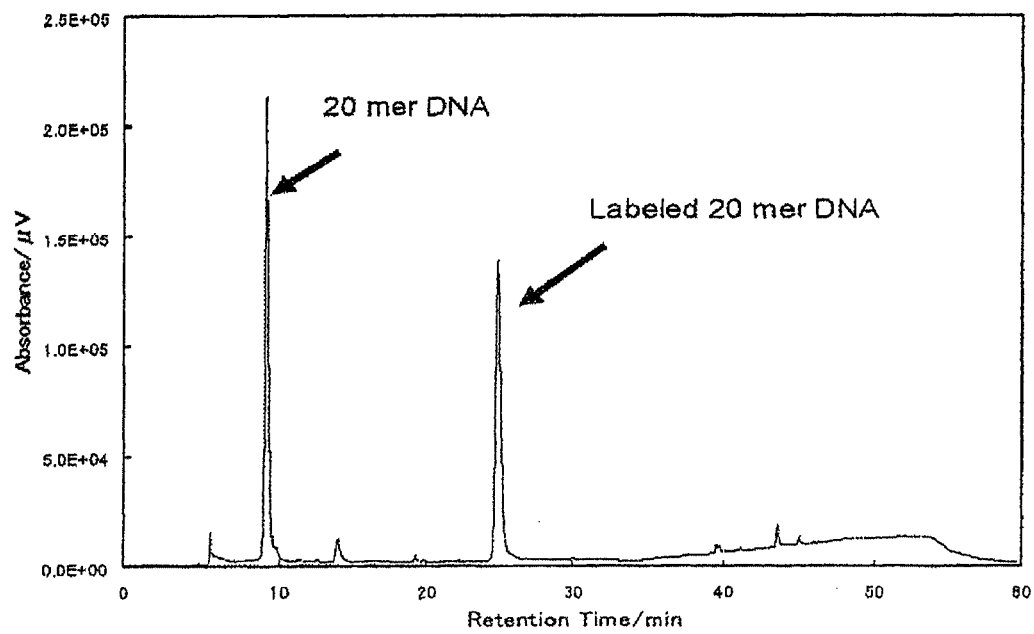
FIG. 5A shows one example of the HPLC profile of a labeled 20 mer DNA with EL-OSu in Example 1 of the present invention.
Figure 5B:
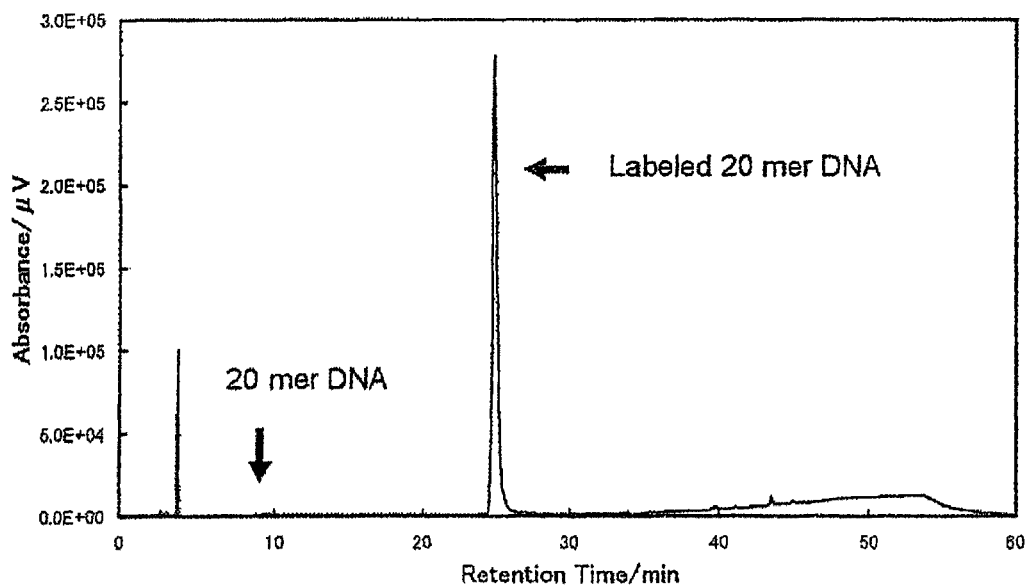
FIG. 5B shows one example of the HPLC profile of a labeled 20 mer DNA with EL-OSu-Sp in Example 1 of the present invention.
Figure 5C:
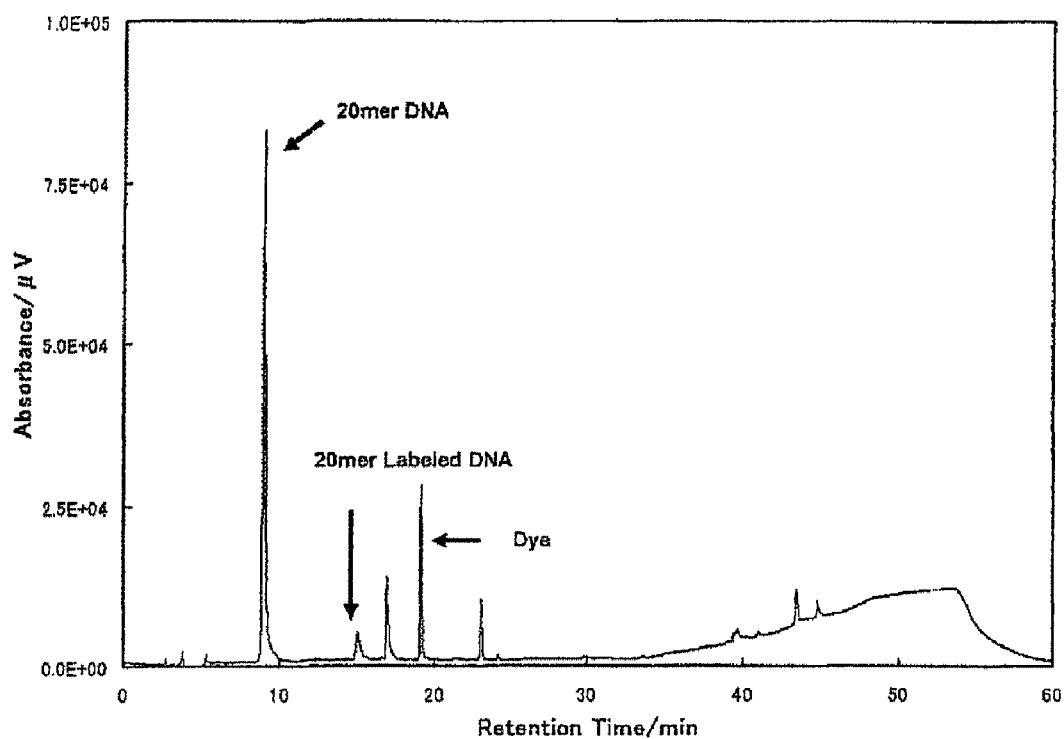
FIG. 5C shows one example of the HPLC profile of a labeled 20 mer DNA with Alexa 594 in Example 1 of the present invention.
Figure 6A:
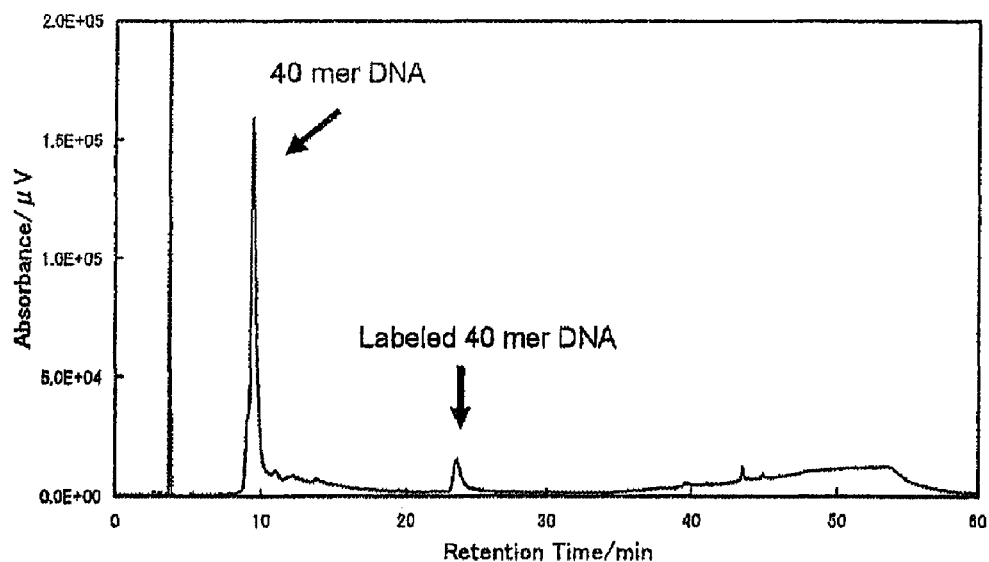
FIG. 6A shows one example of the HPLC profile of a labeled 40 mer DNA with EL-OSu in Example 1 of the present invention.
Figure 6B:
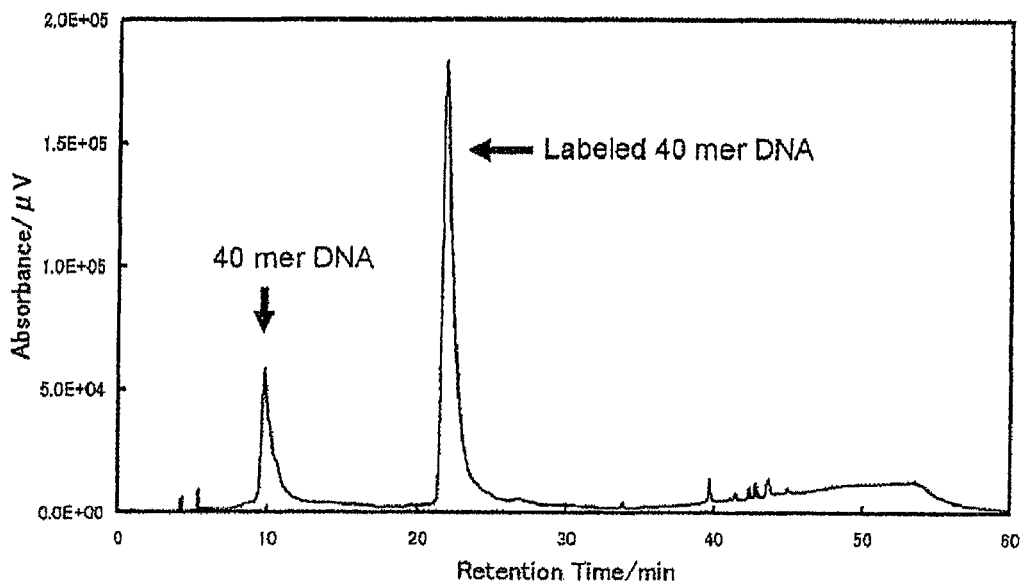
FIG. 6B shows one example of the HPLC profile of a labeled 40 mer DNA with EL-OSu in Example 1 of the present invention.

The HPLC profiles of oligo-DNA labeled with EL-OSu or EL-OSu-Sp are shown in FIG. 4A to 4B for 17 mer DNA, FIG. 5A to 5C for 20 mer DNA and FIG. 6A to 6C for 40 mer DNA. Further, the values of incorporation ratio are shown in Table 1 to 3.

TABLE 1

| | 17mer | |
|---|---|---|
| Active ester | EL-OSu | EL-OSu-Sp |
| mole ratio | 1:1.2 | 1:1.2 |
| Incorporation ratio (%) | 6.1 | 99.1 |

TABLE 2

| | 20mer | | | |
|---|---|---|---|---|
| Active ester | EL-OSu | EL-OSu | EL-OSu-Sp | Alexa594-NHS | Alexa594-NHS |
| mole ratio | 1:1.2 | 1:10 | 1:1.2 | 1:1.2 | 1:10 |
| Incorporation ratio (%) | 11.8 | 54.0 | 99.6 | trace | 5.8 |

TABLE 3

| | 40mer | | |
|---|---|---|---|
| Active ester | EL-OSu | EL-OSu-Sp | EL-OSu-Sp |
| mole ratio | 1:1.2 | 1:1.2 | 1:1.2 |
| Incorporation ratio (%) | 6.1 | 99.1 | 78.0 |

Figure 7:
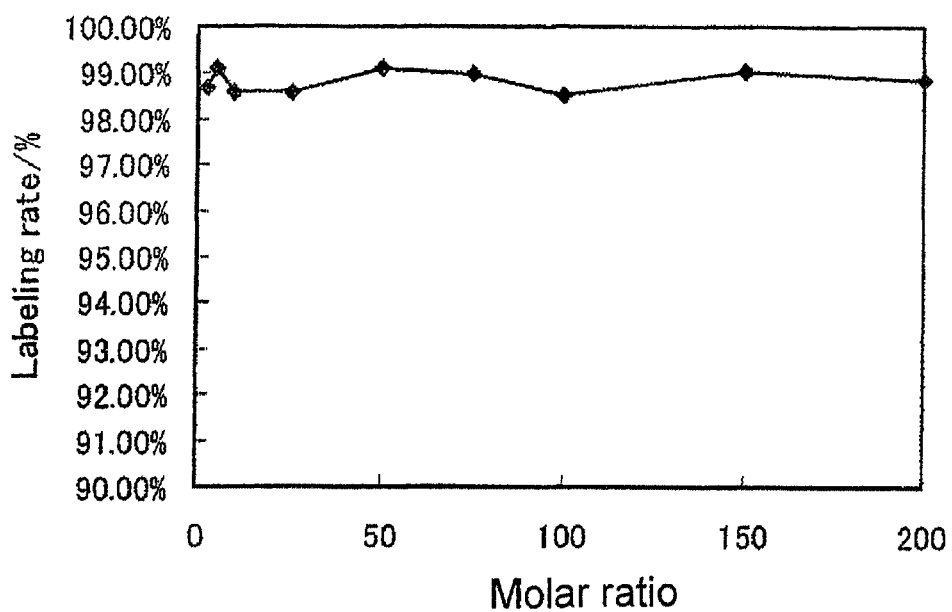
FIG. 7 shows one example of the relationship between the incorporation ration and the additional amount of EL-OSu-Sp.

Next, the change of incorporation ratio when using 17 mer DNA was studied by changing the mixing ratio with EL-OSu-Sp in the following range. The results are shown in FIG. 7.

The incorporation ratio could be increased by using the labeling dye EL-OSu-Sp in which the spacer portion was introduced, comparing with EL-OSu or Alexa 594 having no spacer portion. Especially, when using oligo-DNA having a length of about 20 mer, about 100% of incorporation ratio was obtained by the addition of 1.2-fold mole excess, while in case of EL-OSu, the incorporation ratio was about 12%, and in case of Alexa, the incorporation ratio was trace amount (less than 1%). Although it was difficult to label 17 mer or 40 mer DNA with Alexa, the incorporation ratio of this oligo-DNA could be increased drastically. As almost 100% of the incorporation ratio can be obtained by the addition of 1.2-fold mole excess, it is possible to quantitatively label oligo-DNA with labeling dye EL-OSu-Sp having a spacer portion. Comparing the case of using a conventional labeling dye such as Alexa, in which the incorporation ratio of only about 50% was obtained even by the addition of 200-fold mole excess, the labeling dye EL-OSu-Sp having a spacer portion has a drastic effect that 100% of the incorporation ratio can be obtained by the addition of one in two hundred in case that the oligo-DNA having a length of about 20 mer is used.

Example 2

Labeling of Oligo-DNA with Dye, and Detection Thereof (2)

The labeling conditions are the same as that for Example 1 except that an active ester of imidazolopyridine (5) (Im-EL-OSu-Sp) having a spacer portion was used as an organic EL-dye (Result)

The results are the same as that for an active ester of oxadiazoropyridine (EL-OSu-Sp). About 100% of the incorporation ratio was obtained by the addition of 1.2-fold mole excess.

Example 3

Labeling of Oligo-DNA with Dye, and Detection Thereof (3)

The labeling conditions for 20 mer DNA are the same as that for Example 1 except that an active ester of oxadiazolopyridine (10) having a spacer portion synthesized in Synthesis Example 3 was used an organic EL-dye and 10 μl of DMSO was added so as to be 10 vol % of the total volume of the sample solution.

(Result)

The results are the same as that for an active ester of oxadiazoropyridine (8). About 100% of the incorporation ratio was obtained by the addition of 1.2-fold mole excess. Although in Example 1 DMSO was added so as to be 80 vol % of the total volume of the sample solution in order to dissolve the organic EL-dye, DMSO of 10% of the total volume of the sample solution could dissolve the organic EL-dye and showed superior water-solubility.

Example 4

Labeling of Oligo-DNA with Dye, and Detection Thereof (4)

The labeling conditions for 20 mer DNA are the same as that for Example 1 except that an active ester of oxadiazolopyridine (12) having a spacer portion synthesized in Synthesis Example 4 was used an organic EL-dye and 10 μl of DMSO was added so as to be 10 vol % of the total volume of the sample solution.

(Result)

The results are the same as that for an active ester of oxadiazoropyridine (8). About 100% of the incorporation ratio was obtained by the addition of 1.2-fold mole excess. Further, a superior water-solubility was obtained same as Example 3.

Example 5

Labeling of Oligo-DNA with Dye, and Detection Thereof (5)

The labeling conditions for 20 mer DNA are the same as that for Example 1 except that an active ester of oxadiazolopyridine (14) having a spacer portion synthesized in Synthesis Example 5 was used an organic EL-dye and 10 μl of DMSO was added so as to be 10 vol % of the total volume of the sample solution.

(Result)

The results are the same as that for an active ester of oxadiazoropyridine (8). About 100% of the incorporation ratio was obtained by the addition of 1.2-fold mole excess. Although in Example 1 DMSO was added so as to be 80 vol % of the total volume of the sample solution in order to dissolve the organic EL-dye, DMSO of 10% of the total volume of the sample solution could dissolve the organic EL-dye and showed superior water-solubility.

Example 6

Labeling of Proteins with Dye, and Detection Thereof (1)

(Labeling Procedure)

An amino group of a lysine residue of bovine serum albumin (BSA) and an active ester of oxadiazoropyridine (8) (EL-OSu-Sp) having a spacer portion were reacted to form an amide bond for labeling of BSA. Specifically, to 100 μl of carbonate buffer (pH 9.0) containing 1.0 mg (15.05 nmol) of BSA was added 400 μl of a DMSO solution containing 35.82 μg (75.25 nmol) of the active ester and the mixture was shaken for 24 hours at room temperature. 0.1 M TEAA buffer (pH 7.0) was added so as to give the total volume of 1 ml, and 1.5 ml of components derived from BSA were separated using NAP-10 column (GE Healthcare Sephadex G-25), and 100 μl of the separated solution was analyzed by reverse phase HPLC.

Figure 9A:
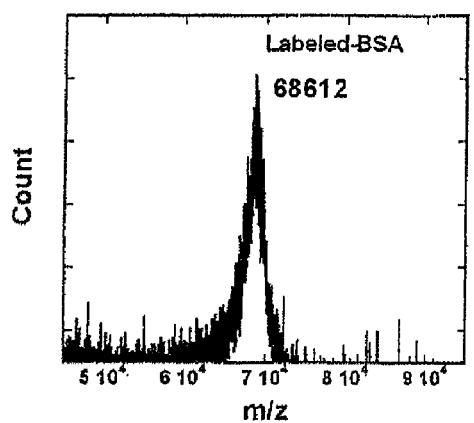
FIG. 9A shows one example of the TOF MS (Time of Flight Mass Spectrometry) spectrum of a labeled BSA with EL-OSu in Example 2 of the present invention.
Figure 9B:
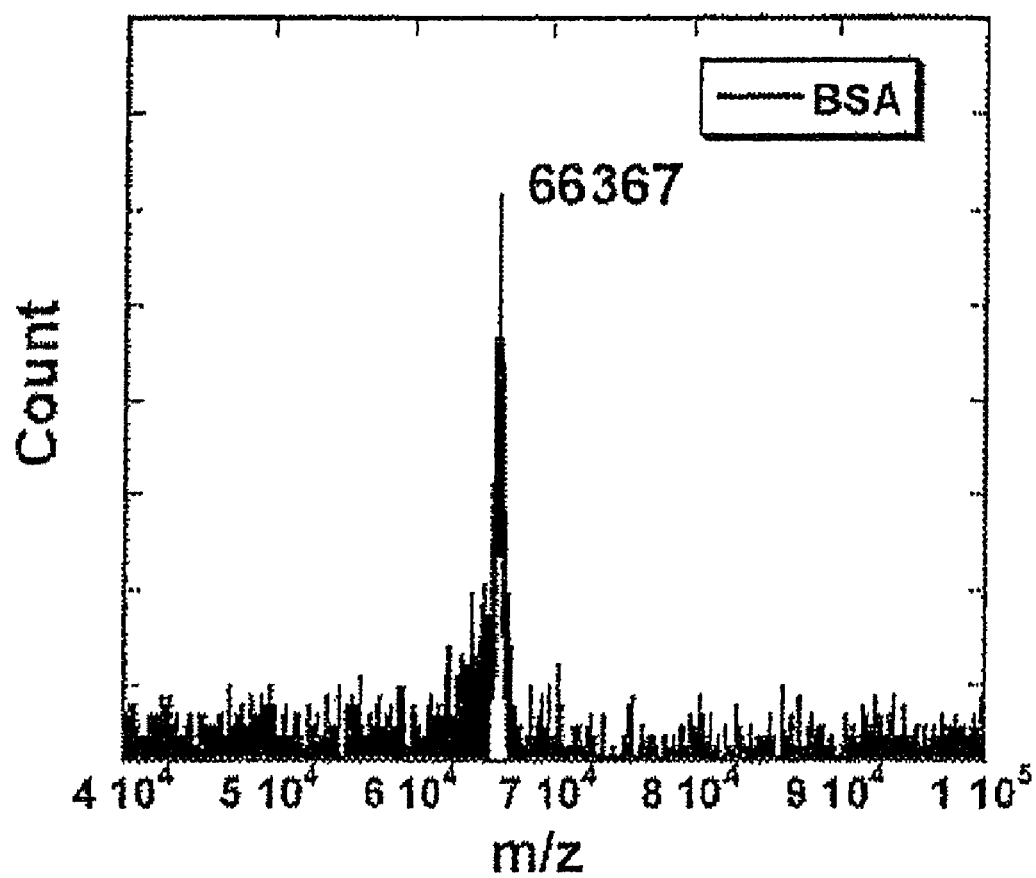
FIG. 9B shows one example of the TOF MS spectrum of BSA before labeling with EL-OSu in Example 2 of the present invention.

Identification of BSA labeled with ELO-OSu was conducted by MALDI TOF MS. As shown in FIG. 9, the labeled BSA (FIG. 9A) had molecular weight increased by about 2200 as compared with the raw material (FIG. 9B), showing that about five organic EL-dyes was bonded thereto.

(HPLC Measurement Conditions)

As a HPLC apparatus, LC-2000plus series of JASCO Corporation was used.
Column: GL Science Inertsil ODS-3 Column 5 μm, 4.6 mm×250 mm
Gradient conditions of HPLC measurement
Eluent solvent A: 0.1 M TEAA solution (pH 7.0)
Eluent solvent B: 90% $CH_3CN$/0.1 M TEAA solution (pH 7.0)
Gradient (B %) 0 min (5%)->20 min (50%)->60 min (70%)->70 min (100%)->80 min (100%)->90 min (5%)
Flow rate 0 min->20 min, 60 min->90 min: 1 ml/min, 20 min->60 min: 0.5 ml/min
Temperature: 4° C.

Figure 8A:
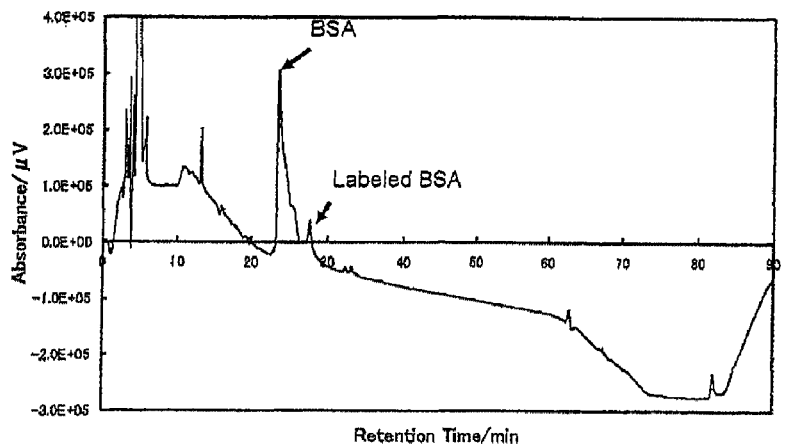
FIG. 8A shows one example of the HPLC profile of a labeled BSA with EL-OSu in Example 2 of the present invention.
Figure 8B:
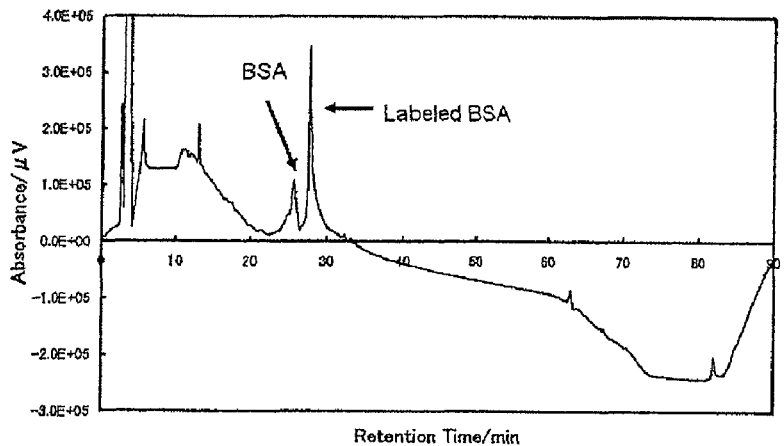
FIG. 8B shows one example of the HPLC profile of a labeled BSA with EL-OSu-Sp in Example 2 of the present invention.

The HPLC profiles of oligo-DNA labeled with EL-OSu having no spacer portion and EL-OSu-Sp having a spacer portion are shown in FIGS. 8A and 8B, respectively. Further, the values of incorporation ratio are shown in Table 4.

TABLE 4

| | BSA | |
|---|---|---|
| Active ester | EL-OSu | EL-OSu-Sp |
| mole ratio | 1:5 | 1:5 |
| Incorporation ratio (%) | 12.5 | 909 |

When reacting with BSA, the incorporation ratio could be drastically increased by using EL-OSu-Sp having a spacer portion instead of EL-OSu having no spacer portion. It is considered that by introducing the spacer portion between an active ester of reactive group and dye molecule, the steric hindrance between the labeling site of BSA and dye molecule can be decreased, and thereby to increase the incorporation ratio. It was confirmed that about five molecule of organic EL-dyes was bonded to BSA labeled with EL-OSu by the result of TOF-MASS. In case of EL-OSu-Sp, BSA was almost quantitatively labeled by the addition of 5-fold mole excess so as to introduce 5 molecules.

Example 7

Labeling of Proteins with Dye, and Detection Thereof (2)

The labeling conditions for BSA are the same as that for Example 5 except that an active ester of oxadiazolopyridine (10) having a spacer portion synthesized in Synthesis Example 3 was used an organic EL-dye and 10 μl of DMSO was added so as to be 10 vol % of the total volume of the sample solution.

(Result)

The results are the same as that for Example 5. Although in Example 5 DMSO was added so as to be 80 vol % of the total volume of the sample solution in order to dissolve the organic EL-dye, in this Example DMSO of 10% of the total volume of the sample solution could dissolve the organic EL-dye and showed superior water-solubility.

Example 8

Labeling of Proteins with Dye, and Detection Thereof (4)

The labeling conditions for BSA are the same as that for Example 5 except that an active ester of oxadiazolopyridine (12) having a spacer portion synthesized in Synthesis Example 4 was used an organic EL-dye and 10 μl of DMSO was added so as to be 10 vol % of the total volume of the sample solution.

(Result)

The results are the same as that for Example 5. Further, in this Example a superior water-solubility was obtained same as Example 5.

Example 9

Labeling of Proteins with Dye, and Detection Thereof (5)

The labeling conditions for BSA are the same as that for Example 5 except that an active ester of oxadiazolopyridine (14) having a spacer portion synthesized in Synthesis Example 5 was used an organic EL-dye and 10 μl of DMSO was added so as to be 10 vol % of the total volume of the sample solution.

(Result)

The results are the same as that for Example 5. Although in Example 5 DMSO was added so as to be 80 vol % of the total volume of the sample solution in order to dissolve the organic EL-dye, in this Example DMSO of 10% of the total volume of the sample solution could dissolve the organic EL-dye and showed superior water-solubility.

Example 10

Labeling of Proteins with Dye, and Detection Thereof (6)

The labeling conditions for BSA are the same as that for Example 5 except that an active ester of oxadiazolopyridine (17) having a spacer portion synthesized in Synthesis Example 6 was used an organic EL-dye and 10 µl of DMSO was added so as to be 10 vol % of the total volume of the sample solution.
(Result)

The results are the same as that for Example 5. Further, a superior water-solubility was also obtained in this Example As explained above, according to the labeling dye of the present invention, it is possible to drastically decrease the amount of dye for labeling the target molecule not only for providing high fluorescence intensity in solid state. For example, it is generally conceived that in case of the conventional dye, about 200-fold mole excess of dye is required for labeling. However, the labeling dye of the present invention can decrease the amount to about one in two hundred. Accordingly, much amount of labeling dye can be decreased, and thereby to deeply cut in the cost for detecting the target molecule. Furthermore, after labeling reaction, as a process to remove the unreacted labeling dye is not needed, it is possible to carry out the detection method more quickly.

The invention claimed is:

1. A labeling dye used for detecting a biomolecule by measurement of fluorescence, wherein the dye comprises a coloring portion comprising an organic EL-dye, a bonding portion to be bonded with the biomolecule and a spacer portion for linking the coloring portion and the bonding portion, wherein said spacer portion is represented by the following general formula (I)

$$-(CHR')_p-X-(CHR'')_q- \qquad (I)$$

wherein X represents a direct bond, or at least one functional group selected from the group consisting of —NHCOO—, —CONH—, —COO—, —SO$_2$NH—, —HN—C(=NH)—NH—, —O—, —S—, —NR—, —CH=CH—, —C≡C—, —AR— and —CO—Ar—NR—; R' and R'' each independently represent a hydrogen atom, an aliphatic hydrocarbon group, or an aromatic hydrocarbon group, and wherein the aliphatic hydrocarbon group or the aromatic hydrocarbon group is optionally substituted with any one charge group selected from the group consisting of a sulfonyl group, hydroxyl group, quaternary ammonium group and carboxyl group; Ar represents an aryl group; and p and q each independently represent an integer of 0 to 20, wherein the value of "p+q" is greater than or equal to 1.

2. A labeling dye used for detecting a biomolecule by measurement of fluorescence, wherein the dye comprises a coloring portion comprising an organic EL-dye, a bonding portion to be bonded with the biomolecule and a spacer portion for linking the coloring portion and the bonding portion, wherein said spacer portion is an amino acid or a peptide linker comprising 2 to 20 amino acids.

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Synthetic Construct; synthetic oligonucleotide

<400> SEQUENCE: 1 act cca gtg gta atc ta                                              17

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct; synthetic oligonucleotide

<400> SEQUENCE: 2 act cca gtg gta atc tac tg                                          20

<210> SEQ ID NO 3
<211> LENGTH: 40
<212> TYPE: DNA
<213> ORGANISM: Artificial Sequence
<220> FEATURE:
<223> OTHER INFORMATION: Synthetic Construct; synthetic oligonucleotide

<400> SEQUENCE: 3 act cca gtg gta atc tac tgg gac gga aca gct ttg agg t               40
```

3. The labeling dye according to claim 1, wherein said organic EL-dye comprises a condensed poly-ring compound consisting of a 5-membered ring compound containing one or more hetero atom(s), selenium atom(s) or boron atom(s) and a 6-membered ring compound having a conjugate system.

4. The labeling dye according to claim 2, wherein said organic EL-dye comprises a condensed poly-ring compound consisting of a 5-membered ring compound containing one or more hetero atom(s), selenium atom(s) or boron atom(s) and a 6-membered ring compound having a conjugate system.

5. The labeling dye according to claim 2, wherein said condensed poly-ring compound is an azole derivative of the following general formula (1), (2) or (3):

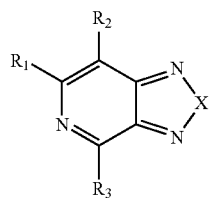
(1)

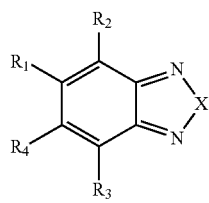
(2)

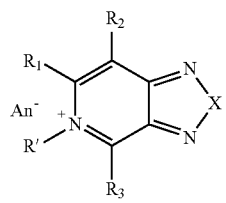
(3)

wherein, $R_1$, $R_2$, $R_3$ and $R_4$ each independently represent a hydrogen atom, an aromatic hydrocarbon group, hydrocarbon group, heterocyclic group or aromatic group containing a hetero atom in the ring, optionally having a substituent; X represents a nitrogen atom, sulfur atom, oxygen atom, selenium atom or boron atom; R' represents an aliphatic hydrocarbon group, optionally having a substituent, or an aromatic hydrocarbon group; and $An^-$ represents a halide ion.

6. The labeling dye according to claim 5, wherein $R_2$ and $R_3$ each independently represent any one compound selected from the group consisting of a thiophene derivative, furan derivative, pyrole derivative, imidazole derivative, oxazole derivative, thiazole derivative and pyridine derivative.

7. The labeling dye according to claim 5, wherein $R_2$ and $R_3$ represent an aryl group having a sulfonyl group.

8. The labeling dye according to claim 2, wherein said condensed poly-ring compound is an imidazole derivative of the following general formula (4), (5), (6), (7) or (8):

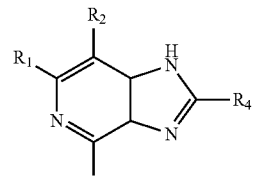
(4)

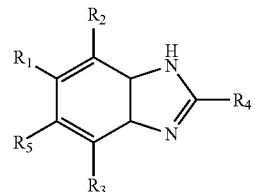
(5)

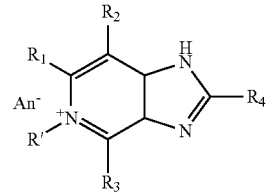
(6)

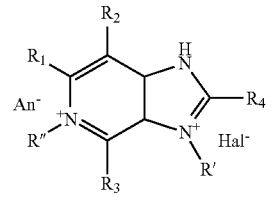
(7)

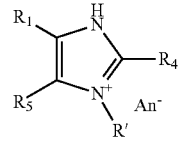
(8)

wherein, $R_1$, $R_2$, $R_3$, $R_4$ and $R_5$ each independently represent a hydrogen atom, an aromatic hydrocarbon group, hydrocarbon group, heterocyclic group or aromatic group containing a hetero atom in the ring, optionally having a substituent; $R_1$, $R_2$, $R_3$, $R_4$ and $R_5$ may be the same or different; R' and R" represent an aliphatic hydrocarbon group, optionally having a substituent, or an aromatic hydrocarbon group; and An represents a halide ion.

9. The labeling dye according to claim 8, wherein $R_2$ and $R_3$ each independently represent any one compound selected from the group consisting of a thiophene derivative, furan derivative, pyrole derivative, imidazole derivative, oxazole derivative, thiazole derivative and pyridine derivative.

10. The labeling dye according to claim 8, wherein $R_2$ and $R_3$ represent an aryl group having a sulfonyl group.

11. The labeling dye according to claim 1, wherein said bonding portion is any one reactive group selected from the group consisting of a carboxyl group, isocyanate group, isothiocyanate group, epoxy group, halogenated alkyl group, triazine group, carbodiimide group and active ester carbonyl group.

12. The labeling dye according to claim 2, wherein said bonding portion is any one reactive group selected from the group consisting of a carboxyl group, isocyanate group, isothiocyanate group, epoxy group, halogenated alkyl group, triazine group, carbodiimide group and active ester carbonyl group.

13. The labeling dye according to claim 2, wherein said spacer is a natural amino acid or synthetic amino acid.

14. The labeling dye according to claim 13, wherein said amino acid is any one selected from the group consisting of cysteine acid, 2-amino-sulfosulfanylpropanic acid, 2-amino-amino-3-sulfoxypropanic acid, tyrosine, threonine, 4-amino-2-hydroxybutanic acid, homo-serine and serine.

15. The labeling dye according to claim 2, wherein said spacer is a peptide linker comprising at least one charge group selected from the group consisting of a sulfonyl group, hydroxyl group, quaternary ammonium group and carboxyl group.

16. The labeling dye according to claim 15, wherein said peptide linker comprises at least one amino acid selected from the group consisting of cysteine acid, 2-amino-sulfosulfanyl-propanic acid, 2-amino-amino-3-sulfoxypropanic acid, tyrosine, threonine, 4-amino-2-hydroxybutanic acid, homo-serine and serine.

17. A labeling kit used to detect a biomolecule by fluorescence measurement, wherein said labeling kit includes a labeling dye comprising a coloring portion comprising an organic EL-dye, a bonding portion to be bonded with a biomolecule and a spacer portion for linking the coloring portion and the bonding portion,
wherein said spacer portion is represented by the following general formula (I)

$$—(CHR)_p—X—(CHR'')_q— \quad (I)$$

wherein X represents a direct bond, or at least one functional group selected from the group consisting of —NHCOO—, —CONH—, —COO—, —SO$_2$NH—, —HN—C(=NH)—NH—, —O—, —S—, —NR—, —CH=CH—, —C≡—, —Ar— and —CO—Ar—NR—; R' and R'' each independently represent a hydrogen atom, an aliphatic hydrocarbon group, or an aromatic hydrocarbon group, and wherein the aliphatic hydrocarbon group or the aromatic hydrocarbon group is optionally substituted with any one charge group selected from the group consisting of a sulfonyl group, hydroxyl group, quaternary ammonium group and carboxyl group; Ar represents an aryl group; and p and q each independently represent an integer of 0 to 20, wherein the value of "p+q" is greater than or equal to 1.

18. A labeling kit used to detect a biomolecule by fluorescence measurement, wherein said labeling kit includes a labeling dye comprising a coloring portion comprising an organic EL-dye, a bonding portion to be bonded with a biomolecule and a spacer portion for linking the coloring portion and the bonding portion,
wherein said spacer portion is an amino acid or a peptide linker comprising 2 to 20 amino acids.

19. The labeling kit according to claim 17, said labeling kit comprising a reactive group introducing reagent to introduce a reactive group into the labeling dye selected from the group consisting of a carboxyl group, isocyanate group, isothiocyanate group, epoxy group, halogenated alkyl group, triazine group, carbodiimide group and active ester carbonyl group.

20. The labeling kit according to claim 18, said labeling kit comprising a reactive group introducing reagent to introduce a reactive group into the labeling dye selected from the group consisting of a carboxyl group, isocyanate group, isothiocyanate group, epoxy group, halogenated alkyl group, triazine group, carbodiimide group and active ester carbonyl group.

21. A method of detecting a biomolecule, comprising reacting the biomolecule with a labeling dye comprising a coloring portion including an organic EL-dye, a bonding portion to be bonded with a biomolecule and a spacer portion for linking the coloring portion and the bonding portion, and measuring the fluorescence of the labeled biomolecule,
wherein said spacer portion is represented by the following general formula (I)

$$—(CHR)_p—X—(CHR'')_q— \quad (I)$$

wherein X represents a direct bond, or at least one functional group selected from the group consisting of —NHCOO—, —CONH—, —COO—, —SO$_2$NH—, —HN—C(=NH)—NH—, —O—, —S—, —NR—, —CH=CH—, —C≡—, —Ar— and —CO—Ar—NR—; R' and R'' represent each independently a hydrogen atom, an aliphatic hydrocarbon group, or an aromatic hydrocarbon group, and wherein the aliphatic hydrocarbon group or the aromatic hydrocarbon group is optionally substituted with any one charge group selected from the group consisting of a sulfonyl group, hydroxyl group, quaternary ammonium group and carboxyl group; Ar represents an aryl group; and p and q each independently represent an integer of 0 to 20, wherein the value of "p+q" is greater than or equal to 1.

22. A method of detecting a biomolecule, comprising reacting the biomolecule with a labeling dye comprising a coloring portion including an organic EL-dye, a bonding portion to be bonded with a biomolecule and a spacer portion for linking the coloring portion and the bonding portion, and measuring the fluorescence of the labeled biomolecule,
wherein said spacer portion is an amino acid or a peptide linker comprising 2 to 20 amino acids.

23. The method according to claim 21, wherein said biomolecule is any one selected from the group consisting of nucleic acids, proteins, peptides and saccharides.

24. The method according to claim 22, wherein said biomolecule is any one selected from the group consisting of nucleic acids, proteins, peptides and saccharides.

* * * * *